(12) United States Patent
Tokuyama et al.

(10) Patent No.: US 9,381,146 B2
(45) Date of Patent: Jul. 5, 2016

(54) SKIN CONDITIONER

(75) Inventors: Takashi Tokuyama, Ayauta-gun (JP); Megumi Jo, Ayauta-gun (JP)

(73) Assignee: Kabushiki Kaisha Soken, Kagawa (JP)

( * ) Notice: Subject to any disclaimer, the term of this patent is extended or adjusted under 35 U.S.C. 154(b) by 0 days.

(21) Appl. No.: 13/013,316

(22) Filed: Jan. 25, 2011

(65) Prior Publication Data

US 2011/0213033 A1    Sep. 1, 2011

Related U.S. Application Data

(63) Continuation of application No. 12/454,447, filed on May 18, 2009, now abandoned, which is a continuation of application No. 10/771,735, filed on Feb. 4, 2004, now abandoned, which is a continuation of application No. 10/680,331, filed on Oct. 7, 2003, now abandoned, which is a continuation of application No. 09/623,968, filed as application No. PCT/JP99/01161 on Mar. 10, 1999, now abandoned.

(30) Foreign Application Priority Data

Mar. 11, 1998 (JP) .................................. 10-103280

(51) Int. Cl.
*A61K 36/899* (2006.01)
*A61K 8/41* (2006.01)
*A61K 8/44* (2006.01)
*A61Q 19/00* (2006.01)

(52) U.S. Cl.
CPC ... *A61K 8/41* (2013.01); *A61K 8/44* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 4,507,321 A | 3/1985 | Raisfeld | |
| 4,704,473 A * | 11/1987 | Nakamura et al. | 562/463 |
| 5,079,003 A | 1/1992 | Scaffidi | |
| 5,126,136 A | 6/1992 | Merat et al. | |
| 5,128,375 A | 7/1992 | Tanaka et al. | |
| 5,143,518 A | 9/1992 | Madrange et al. | |
| 5,571,518 A | 11/1996 | Pillai et al. | |
| 5,753,214 A | 5/1998 | Yoshioka et al. | |
| 5,876,736 A | 3/1999 | Cohen et al. | |
| 5,925,365 A | 7/1999 | Yamamoto | |
| 5,952,000 A | 9/1999 | Venkateshwaran et al. | |
| 6,008,246 A | 12/1999 | Ito et al. | |
| 6,017,520 A | 1/2000 | Synodis et al. | |
| 6,063,391 A | 5/2000 | Nanba et al. | |
| 6,497,898 B1 | 12/2002 | Ikemoto et al. | |
| 6,528,068 B1 | 3/2003 | Yumioka et al. | |
| 6,821,780 B2 | 11/2004 | Thorel et al. | |
| 6,951,658 B1 | 10/2005 | Pearson et al. | |

FOREIGN PATENT DOCUMENTS

| | | |
|---|---|---|
| EP | 0 576 748 | 1/1994 |
| EP | 0 842 655 | 5/1998 |
| JP | 362298509 | 12/1987 |
| JP | 63159304 A * | 7/1988 |
| JP | 363159304 | 7/1988 |
| JP | 63264511 A * | 11/1988 |
| JP | 63264511 A * | 11/1988 |
| JP | 04-095008 | 3/1992 |
| JP | 04095008 A * | 3/1992 |
| JP | 5-310549 | 11/1993 |
| JP | 6-122611 | 5/1994 |
| JP | 4-619206 | 7/1994 |
| JP | 6-189780 | 7/1994 |
| JP | 07097312 A * | 4/1995 |
| JP | 07097312 A * | 4/1995 |
| JP | 07-252129 | 10/1995 |
| JP | 8-217695 | 8/1996 |
| JP | 8-268866 | 10/1996 |
| JP | 9-95414 | 4/1997 |
| JP | 9-95415 | 4/1997 |
| JP | 9-505822 | 6/1997 |
| JP | 9-505823 | 6/1997 |

(Continued)

OTHER PUBLICATIONS

DW-1990-302836, Aug. 28, 1990, DW.
DW-1995-228634, May 30, 1995, DW.
DW-1983-60591, Nov. 30, 1982, DW.
XP002277444—Database WPI, Section CH, Week 199423, Derwent Publications Ltd., London, GB; Class A96, AN 1994-186346.

(Continued)

*Primary Examiner* — Chris R Tate
*Assistant Examiner* — Randall Winston
(74) *Attorney, Agent, or Firm* — Norris McLaughlin & Marcus, P.A.

(57) ABSTRACT

The present invention relates to a skin conditioner comprising the compound represented with the general formula:

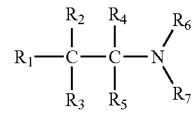

(wherein, the symbols are the same as those defined in the text). Examples of active ingredients of the present invention include L-arginine and ethanolamine. These active ingredients can be acquired as chemical synthesis products, or they may also be acquired in the form of natural substances. Preferable examples of natural substances include substances containing L-arginine and/or ethanolamine obtained from rice. The skin conditioner as claimed in the present invention demonstrates remarkable effectiveness as an agent for the prevention and treatment of atopic dermatitis and as a skin moisture retention agent.

5 Claims, 34 Drawing Sheets

(56) References Cited

FOREIGN PATENT DOCUMENTS

| | | |
|---|---|---|
| JP | 9-175983 | 7/1997 |
| JP | 9-241156 | 9/1997 |
| JP | 9-255550 | 9/1997 |
| JP | 10-1410 | 1/1998 |
| JP | 10-203920 | 8/1998 |
| JP | 4-102453 | 9/1998 |
| JP | 7-233046 | 9/1998 |
| JP | 10-273413 | 10/1998 |
| JP | 10-513452 | 12/1998 |
| JP | 11-100320 | 4/1999 |
| WO | WO-93/18760 | 9/1993 |
| WO | WO-95/15148 | 6/1995 |
| WO | WO-96/21421 | 7/1996 |
| WO | WO-99/45900 | 9/1999 |

OTHER PUBLICATIONS

Database WPI, Derwent-Acc-No. 1995-175320, Week 199523, Copyright 2007 Derwent Information Ltd.
Jan. 1, 1997 "Antioxidative and Metal-Chelating Effects of Polyamines." Erik Lovaas. Advances in Pharmacology. vol. 38. pp. 119-149.
Jan. 1, 1995 "Hypothesis: Spermine May be an Important Epidermal Antioxidant." E. Lovaas Medical Hypotheses vol. 45 pp. 59-67.
Jan. 1, 1989 "Skin again and photoaging: An overview." Barbara A. Gilchrest. Journal of the American Academy of Dermatology. vol. 21 pp. 610-613.
Jan. 1, 1978 Fermentation Technology. vol. 56, No. 6 pp. 745-751.
Feb. 1, 1993 Fragrance Journal. pp. 42-45.
DW-1995-308996, Aug. 8, 1995, DW.
DW-1995-175320, Apr. 11, 1995, DW.

* cited by examiner

Recovery test for collagen production in fibroblasts

Chapped skin recovery test

Overall improvement (usefulness)

Improvement of itchiness, induration and cornification

Improvement of scaling and cracking

Improvement of erythema, dryness and wrinkles

Overall improvement (usefulness)

Improvement of itchiness, induration and cornification

Improvement of scaling and cracking

Improvement of erythema, dryness, and wrinkles

Inflammatory changes ... dermal tissue

Inflammatory changes in dermal tissue

Inflammatory changes in epidermal tissue

Inflammatory changes in epidermal tissue

Moisture retention duration test

Moisture retention duration test

Fig. 35 Transepidermal moisture evaporation volume

Change in improvement

Overall improvement
(N=12)

Change in improvement

Overall improvement
(N=7)

Change in improvement

Overall improvement

SKIN CONDITIONER

REFERENCE TO RELATED APPLICATION

This is a continuation application of Ser. No. 12/454,447, filed May 18, 2009, currently pending, which is in turn, a continuation of Ser. No. 10/771,735, filed Feb. 4, 2004, currently abandoned, which is in turn, a continuation of Ser. No. 10/680,331, filed Oct. 7, 2003, currently abandoned, which is in turn, a continuation of Ser. No. 09/623,968, filed Sep. 11, 2000, currently abandoned. The subject matter of the aforementioned prior applications is hereby incorporated herein by reference.

BACKGROUND OF THE INVENTION

The present invention relates to a skin conditioner that can be used in a broad range of fields including cosmetics, over-the-counter pharmaceuticals and pharmaceuticals.

In addition to that resulting from aging, human skin and scalp have recently become constantly exposed to risks from external factors such as ultraviolet rays, drying, air-conditioning, air pollution, other irritants and microorganisms, and from internal factors such as contamination by food, water or agricultural chemicals and additives through them, as well as sleep, fatigue and stress.

As a result of these risks, there are many persons with unhealthy skin or persons having skin that at first appears healthy, but is actually in a functionally or structurally unhealthy state. Even persons of an age who ought to inherently have healthy skin have skin that requires the use of cosmetics. However, typical moisture retention agents and oils used in current cosmetics are known to only reach the surface of the skin, and only function as a moisture covering or oil covering without actually acting on the skin.

On the other hand, although oils such as Vaseline have long been used for treatment of symptoms and diseases caused by drying of the skin, these are also merely applied to the surface of the skin, thereby forcing the affected person to wait for the symptoms or disease to heal naturally. In addition, since the effects of typical drugs only act on the particular symptom and do not promote the health of the skin itself, in environments like those found at present, if confronted with the same cause after use is discontinued, there are many cases in which the symptom or disease recurs. In addition, drugs also constantly present the risk of being accompanied by adverse side effects.

SUMMARY OF THE INVENTION

Currently in the field of dermatology, it has become an established theory around the world that the corneal layer of the epidermis is responsible for the barrier mechanism that protects the body from the outside world. Therefore, we felt that restoring the skin to its inherently healthy state is the basis of beauty as well as the basic measure for protecting the body from all types of diseases of the skin. In order to accomplish this, the object of the present invention is to condition the corneal layer, condition the entire epidermis and finally condition all skin tissue including the dermis.

In order to accomplish the above object of the present invention, the invention of claim 1 provides a skin conditioner containing one type or two or more types of a compound represented with the following general formula (1):

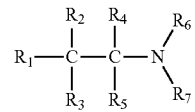

(wherein, $R_1$ represents a hydroxyl group, lower alkoxy group that may optionally have a substituent, a phosphoryloxy group, an aryl group, an amino group, a sulfonic acid group, a phosphatidyloxy group, a lower alkyl group substituted with a hydroxyl group or an amino group or lower alkyl group substituted with a guanidino group;

$R_2$, $R_3$, $R_4$ and $R_5$ respectively and independently represent a hydrogen atom, lower alkyl group that may or may not be substituted with a hydroxyl group, aryl group that may or may not be substituted with a hydroxyl group, carboxyl group, or $R_4$ and $R_5$ represent groups that together form a carbonyl group with an adjacent carbon atom;

$R_6$ and $R_7$ respectively and independently represent a hydrogen atom, lower alkyl group that may or may not be substituted with a hydroxyl group, lower alkylcarbonyl group, aryl group, aralkyl group, or $R_6$ and $R_7$ represent alkylene groups, which may optionally have a substituent, that together form a five-member ring with an adjacent hydrogen atom; and, nitrogen atoms in the formula may be in a quaternary form with a lower alkyl group).

Lower alkyl groups in the present invention are straight chain or branched alkyl groups having 1-10 carbon atoms, and preferably 1-5 carbon atoms, examples of which include a methyl group and ethyl group. Lower alkoxy groups are those which are derived from the above-mentioned lower alkyl groups, examples of which include a methoxy group and ethoxy group. Aryl groups having 6-18 carbon atoms, and preferably 6-10 carbon atoms, examples of which include a phenyl group and α-naphthyl group. Aralkyl groups are those in which an aryl group is substituted for the above-mentioned lower alkyl group, examples of which include a benzyl group and phenythyl group.

In addition, these groups may or may not be substituted with a substitution group, while preferable examples of substitution groups include a hydroxyl group, amino group and carboxyl group.

The invention of claim 2 provides a skin conditioner wherein the compound represented with general formula (1) is L-arginine.

The invention of claim 3 provides a skin conditioner wherein the compound represented with general formula (1) is ethanolamine.

The invention of claim 4 provides a skin conditioner wherein the compound represented with general formula (1) is a compound selected from the group consisting of 2-methoxyethylamine, O-phosphorylethanolamine, 2-ethylaminoethanol, diethanolamine, 2-dimethylaminoethanol, choline, 2-amino-2-hydroxymethyl-1,3-propanediol, noradrenalin, phenethylamine, ethylenediamine, taurine, phosphatidylethanolamine, N-(2-hydroxyethyl)acetoamide, 2-(benzylamino)ethanol, 3-amino-1-propanol, 2-amino-1-butanol, putrescine, DL-pyroglutamic acid and triethanolamine.

DETAILED DESCRIPTION OF THE INVENTION

TEST EXAMPLE 1

Figure 1:
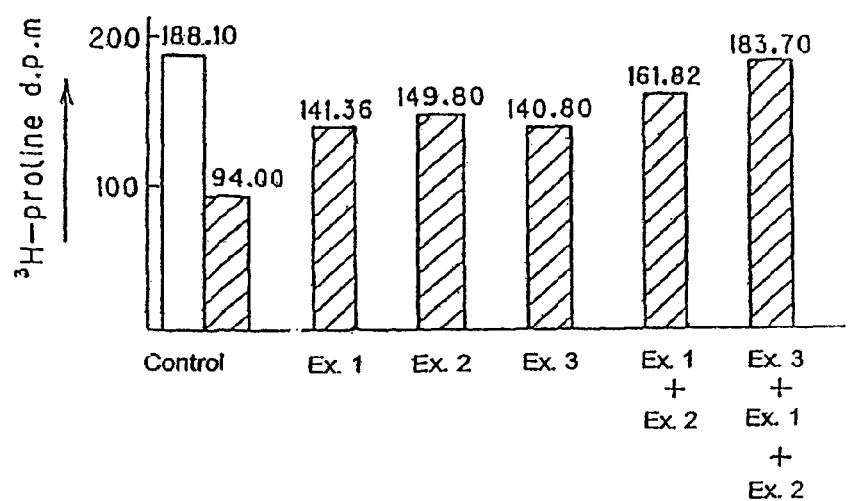
FIG. 1 shows the results of performing a collagen production recovery test on damaged fibroblasts for embodiments of the present invention.

A collagen production recovery test was conducted on damaged fibroblasts.

Fibroblasts are cells that compose the dermis which is on the inside of the skin epidermis. Collagen produced by fibroblasts accounts for approximately 70% of the weight of the dermis, and gives the skin tightness, elasticity and flexibility. In addition, when the skin becomes injured and so forth, it also fulfills the role of the regenerative function of the skin. As the skin ages, the amount of collagen decreases dramatically. Consequently, the skin loses its tightness and elasticity, and wounds are known to heal more slowly. In addition, even in the absence of aging of the skin, the ability to produce collagen decreases due to various causes such as routine exposure to ultraviolet rays and radiation, and the generation of active oxygen.

Samples:

EXAMPLE 1

1% Aqueous Solution of L-arginine (Nakarai Tesk)

EXAMPLE 2

1% Aqueous Solution of Ethanolamine (Nakarai Tesk)

EXAMPLE 3

After crushing 1 kg of rice with a crusher, 250 g of water were mixed in well while spraying followed by allowing to stand for 30 minutes. Next, the rice was boiled for 60 minutes followed by the addition of 2000 mL of water. Moreover, after adding 7.5 g each of α-amylase and β-amylase, the mixture was allowed to stand for 10 hours at 55° C. Next, after gradually raising the temperature and boiling for 5 minutes, the mixture was cooled to 50° C. followed by the addition of 30 g of citric acid, 8 g of acidic protease and 8 g of acidic carboxypeptidase and allowing to react for 24 hours. After completion of the reaction, the mixture was cooled to 20° C. followed by the addition of 200 g of malted rice (*Aspergillus oryzae*) and pre-cultured *Saccharomyces cereviciae* culture broth, and fermenting for 20 days at 20-25° C.

Following completion of fermentation, the mixture was press-filtered to obtain 2700 mL of filtrate. Next, 500 mL of activated charcoal were packed into a column and the filtrate was passed through the column. The resulting effluent was collected to obtain 2700 mL of product containing 1934 mg/L of L-arginine and 162 mg/L of ethanolamine. (The concentration of L-arginine was approximately 0.2%, and that of ethanolamine was approximately 0.02%.)

MIXTURE OF EXAMPLE 1 AND EXAMPLE 2

MIXTURE OF EXAMPLE 1 AND 2 WITH EXAMPLE 3

Test Method:

Six to eight subcultures of normal human skin fibroblasts (Physicochemical Research Institute, Cell Development Bank BIRGB) were used in the test.

Hypoxanthine at a final concentration of 50 μM and 34.5 mU/dish of xanthine oxidase were added to the culture broth to generate active oxygen and lower the collagen production ability of the cells.

Measurement of collagen production ability of a confluent in the steady state was performed according to the method of Webster, et al. based on the uptake of $^3$H-proline into the produced collagen. Furthermore, the samples were mixed with the cells to a final concentration of 3.3% (taking 1% to be 100% for a 1% aqueous solution) and after incubating for 24 hours at 37° C. and 5% $CO_2$, the $^3$H activity taken up into the collagen in the cells was measured.

Reference: Principle of Measurement of Collagen Production Ability

Since proline is a main component of the amino acids that compose collagen, fibroblasts are cultured in a medium containing $^3$H-proline, and the $^3$H activity taken up into collagen in the cells is measured. Units are in d.p.m., and represent the number of daltons of radioactivity released per minute.

Test Results:

As shown in FIG. 1, according to the results of a collagen production recovery test, the collagen production ability of fibroblasts damaged by active oxygen was determined to be significantly improved by L-arginine and ethanolamine. Although L-arginine and ethanolamine are contained in the product of Example 3, since the amounts are excessively small, production was nearly equal to Example 1. When 1% L-arginine and 1% ethanolamine were further added to the product of Example 3, production nearly completely recovered.

Namely, although remarkable recovery is observed with L-arginine or ethanolamine alone, if both L-arginine and ethanolamine are present and their amounts are increased, the collagen production ability of damaged fibroblasts can be nearly completely restored to its original normal level.

TEXT EXAMPLE 2

A moisture retention duration test was conducted.

Moisture retention refers to the peak of the amount of skin moisture (skin electrical conductivity) 15 minutes after application, while moisture retention duration refers to the integral value of a curve indicated by the amount of skin moisture (skin electrical conductivity) from 30 minutes to 120 minutes after application.

Samples:

EXAMPLE 4

1% L-arginine Only Type

| | |
|---|---|
| L-arginine (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 5

1% Ethanolamine Only Type

| | |
|---|---|
| Ethanolamine (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 6

0.2% L-arginine+0.02% Ethanolamine+Simple Preparation

| | |
|---|---|
| Example 3 | 90.00 mL |
| 95% ethanol | 2.00 mL |
| Parabenzene | 0.18 g |
| Purified soy bean lecithin | 0.05 g |

Brought to a final weight of 100.00 g by addition of purified water.

COMPARATIVE EXAMPLE 1

Simple Preparation

| | |
|---|---|
| 95% ethanol | 2.00 mL |
| Parabenzene | 0.18 g |
| Purified soy bean lecithin | 0.05 g |

Brought to a final weight of 100.00 g by addition of purified water.

COMPARATIVE EXAMPLE 2

Hyaluronic Acid+Simple Preparation

| | |
|---|---|
| Hyaluronate (2) | 1.00 g |
| 95% ethanol | 2.00 mL |
| Parabenzene | 0.18 g |
| Purified soy bean lecithin | 0.05 g |

Brought to a final weight of 100.00 g by addition of purified water.

Panelists: 5 healthy volunteers

Test Method: Each sample was applied to the side of the forearm of the panelists (4×4 cm$^2$) followed by measurement of epidermal keratin moisture content at 15, 30, 60, 90 and 120 minutes after application.

Keratin contains salts, amino acids and other electrolytes in addition to moisture. Consequently, although current does not flow through pure water, since electrolytes are contained in keratin in the skin, current flows corresponding to the amount of moisture present is moisture is present. The parameter that is actually measured is electrical conductivity, which is the inverse of the resistance that composes impedance.

Measurement Method:
(1) The test site is washed with soap.
(2) The test site is exposed in a constant temperature and constant humidity room at a temperature of 20° C. and humidity of 50%, and the skin is allowed to reach a steady state by allowing the panelists to rest quietly starting 60 minutes before measurement.
(3) The moisture content of keratin at the test site is measured and used as the value before application.
(4) After uniformly applying 0.03 mL aliquots of sample to the test site four times, the sample is gently wiped off with gauze.

(5) The moisture content of the keratin at the test site 15, 30, 60, 90 and 120 minutes after application, and that of keratin at a site at which sample is not applied in the form of a control, were measured.

Values obtained by subtracting the value before application and value of the site where sample was not applied from the keratin moisture content for each measurement time were taken to represent skin moisture content.

Test Apparatus:

SKICON-200 (IBS Epidermal Keratin Moisture Measuring System (3.5 MHz high-frequency conductivity measuring system))

Figure 2:
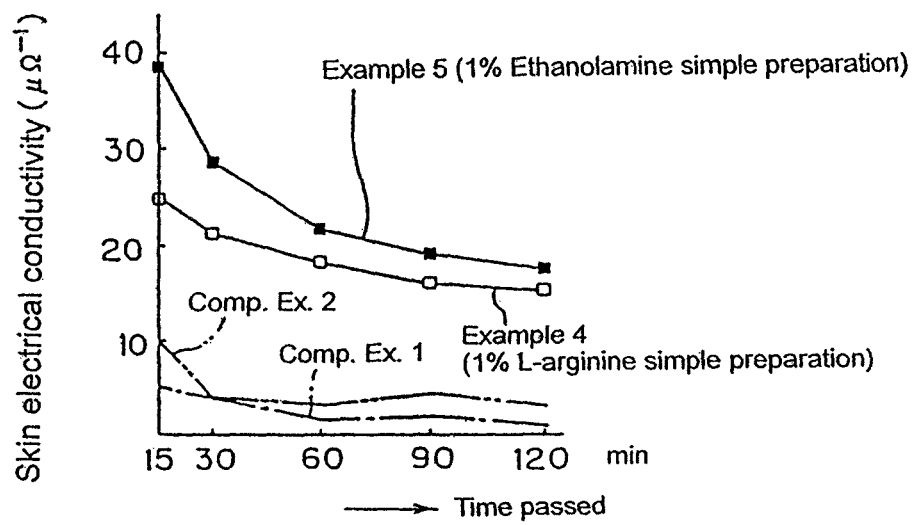
FIG. 2 shows the results of a moisture retention duration test on embodiments of the present invention.
Figure 3:
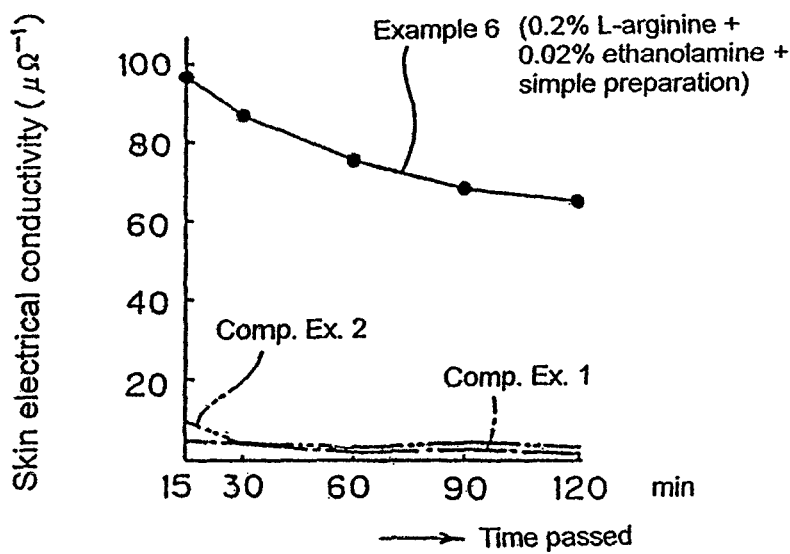
FIG. 3 shows the results of a moisture retention duration test on an embodiment of the present invention.

Test Results:

The results of the moisture retention duration test are as shown in FIGS. 2 and 3.

Although peak values rose even at just 15 minutes after application and moisture retention effects were remarkable for Examples 4, 5 and 6, moisture retention continued beyond 30 minutes and lasted for 2 hours. Although continuation of moisture retention was observed with either L-arginine or ethanolamine alone, when both substances were present, moisture retention duration was enhanced more than when either substance was used alone even at lower concentrations.

On the other hand, although peaks were observed after 15 minutes in the case of Comparative Examples 1 and 2, moisture content returned to its original level after 30 minutes, and continuation of moisture retention was not observed at all.

TEST EXAMPLE 3

A moisture retention ability test was conducted as an indicator of the state of skin health.

Samples:

EXAMPLE 4

L-arginine+Simple Preparation

EXAMPLE 5

Ethanolamine+Simple Preparation

EXAMPLE 6

L-arginine+Ethanolamine+Simple Preparation

EXAMPLE 7

L-arginine+Ethanolamine+Body Soap Preparation

| Example 3 | 20.00 mL |
| Lauric acid | 2.50 g |
| Myristic acid | 7.50 g |
| Palmitic acid | 2.50 g |
| Oleic acid | 2.50 g |
| Lauroyldiethanolamide | 5.00 g |
| Glycerin | 20.00 g |
| Parabenzene | 0.20 g |
| Potassium hydroxide | 3.60 g |
| Edetate | 0.20 g |
| Fragrance | As suitable |

Brought to a final weight of 100.00 g by addition of purified water.

COMPARATIVE EXAMPLE 1

Simple Preparation

COMPARATIVE EXAMPLE 3

| Lauric acid | 2.50 g |
| Myristic acid | 7.50 g |
| Palmitic acid | 2.50 g |
| Oleic acid | 2.50 g |
| Lauroyldiethanolamide | 5.00 g |
| Glycerin | 20.00 g |
| Parabenzene | 0.20 g |
| Potassium hydroxide | 3.60 g |
| Edetate | 0.20 g |
| Fragrance | As suitable |

Brought to a final weight of 100.00 g by addition of purified water.

Subjects: 4 healthy volunteers

Measurement Method:

(1) The test site is washed with soap.

(2) The test site is exposed in a constant temperature and constant humidity room at a temperature of 20° C. and humidity of 50%, and the skin is allowed to reach a steady state by allowing the subjects to rest quietly starting 60 minutes before measurement.

(3) The moisture content of keratin at the test site is measured.

(4) 0.03 mL of distilled water are placed over the test site and wiped off with gauze 10 seconds later followed by measurement of keratin moisture content at the test site immediately, 30, 60, 90 and 120 seconds after wiping off.

(5) 0.03 mL aliquots of sample are applied to the test site three times and allowed to stand for 15 minutes.

(6) The test site is washed carefully.

(7) After 120 minutes, keratin moisture content is measured after 120 seconds by performing the same procedure as in step (4).

Moisture retention ability is determined in the manner indicated below.

Moisture retention ability (%)=[Keratin moisture content 30-120 seconds after moisture loading/Keratin moisture content immediately after moisture loading]×100

Furthermore, moisture retention ability (ratio) was expressed as the ratio obtained when the moisture retention ability before washing (%) is given a value of 1.

Test Apparatus: Same as Test Example 2.

Figure 4:
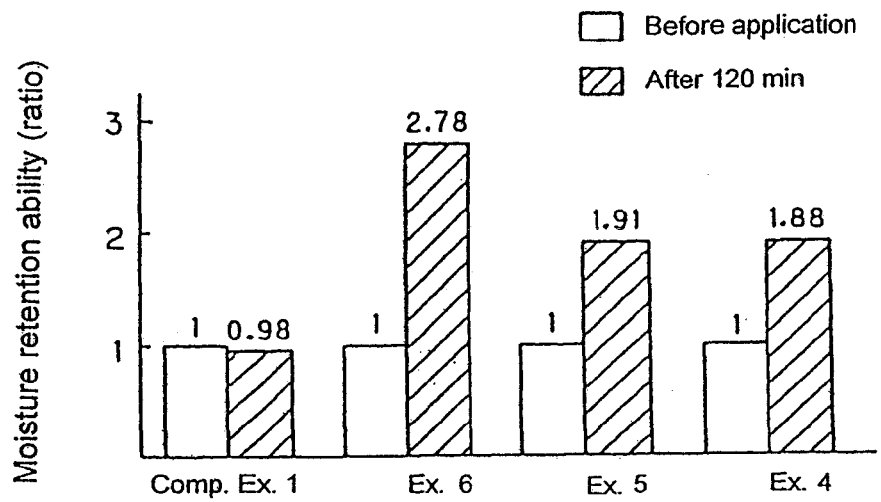
FIG. 4 shows the results of performing a moisture retention ability test on embodiments of the present invention.
Figure 5:
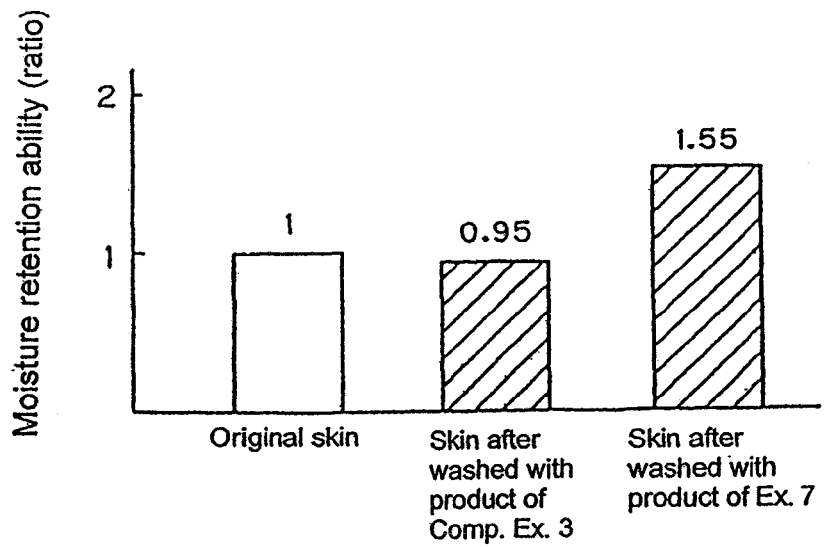
FIG. 5 shows the results of performing a moisture retention ability test on embodiments of the present invention.

Test Results:

The results of the moisture retention ability test are as shown in FIGS. 4 and 5.

Although there was no increase whatsoever in moisture retention ability, which represents the health of the skin, observed for Comparative Example 1, the moisture retention ability 2 hours after application in Examples 4, 5 and 6 increased considerably as compared with the moisture retention ability before application. When the moisture retention ability before application is taken to have a value of 1, although that of Examples 4 and 5 is nearly two times greater, in Example 6, the moisture retention ability increased to nearly three times greater.

In the case of washing with Comparative Example 3, although moisture retention ability decreases as compared with that before washing, washing with Example 7 resulted in an increase in moisture retention ability as compared with before washing.

TEST EXAMPLE 4

A moisture retention duration test was conducted on persons with chapped skin.

Samples:

EXAMPLE 4

L-arginine+Simple Preparation

EXAMPLE 5

Ethanolamine+Simple Preparation

EXAMPLE 6

L-arginine+Ethanolamine+Simple Preparation

COMPARATIVE EXAMPLE 1

COMPARATIVE EXAMPLE 2

Panelists: 6 volunteers with chapped skin

Test Method:

Each sample was applied to the side of the forearm of the panelists (4×4 cm$^2$) followed by measurement of epidermal keratin moisture content at 15, 30, 60, 90 and 120 minutes after application.

Measurement Method: Same as measurement method of Test Example 2.

Determination of Skin Moisture Content: Same as Test Example 2.

Test Apparatus: Same as Test Example 2.

Figure 6:
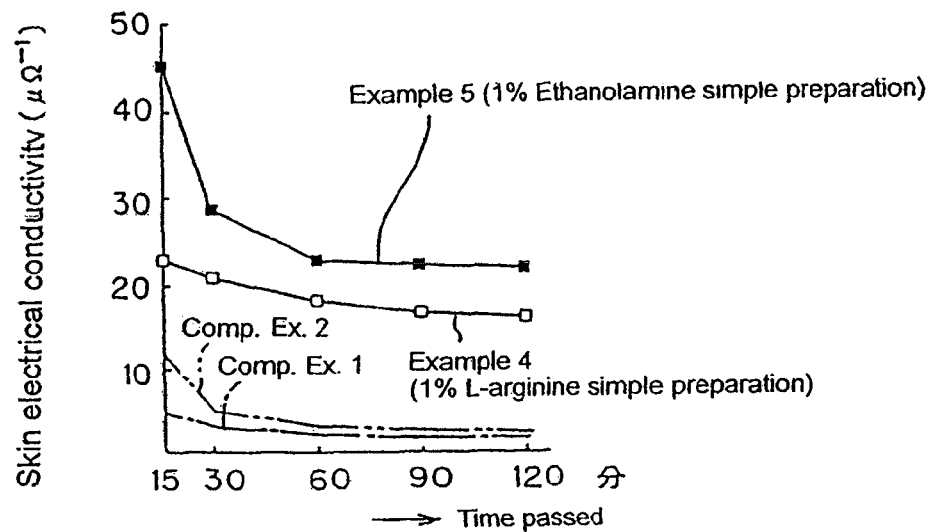
FIG. 6 shows the results of a 2-hour moisture retention duration test according to embodiments of the present invention.
Figure 7:
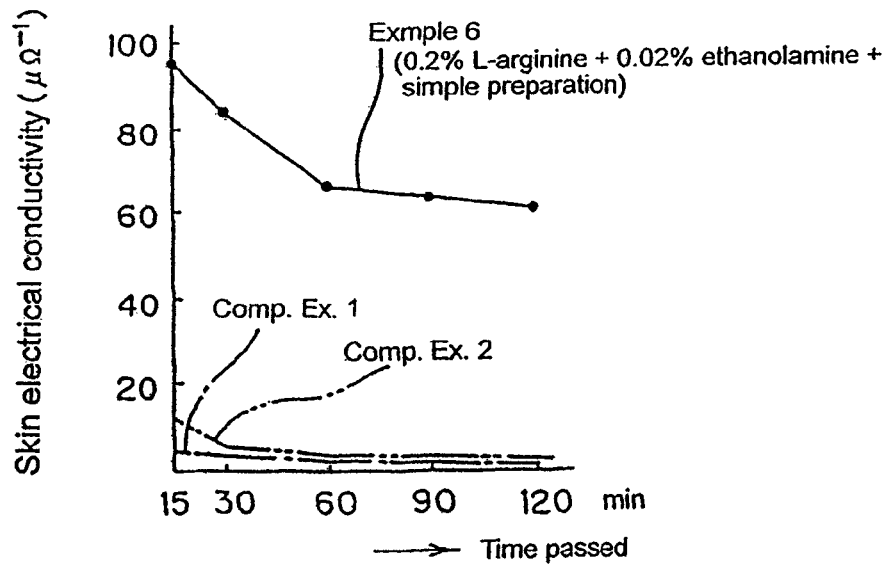
FIG. 7 shows the results of a 2-hour moisture retention duration test according to embodiments of the present invention.

Test Results:

As shown in FIGS. 6 and 7, although the peaks increased and moisture retention effects were remarkable after 15 minutes for Examples 4, 5 and 6, moisture retention continued beyond 30 minutes and lasted for 2 hours. Although this continuation of moisture retention was also observed in Examples 4 and 5, the duration of moisture retention was even greater in Example 6 that contained both L-arginine and ethanolamine.

In Comparative Example 2, although a peak was observed after 15 minutes and moisture retention effects were observed, moisture content returned to its original level after 30 minutes, and continuation of moisture retention with respect to chapped skin was not observed at all.

TEST EXAMPLE 5

Chapped skin was induced artificially and a recovery test was conducted to observe the effects against damaged skin (skin susceptible to both external and internal irritation).

Samples:

EXAMPLE 6

L-arginine+Ethanolamine+Simple Preparation

EXAMPLE 8

L-arginine+Ethanolamine+Cream Preparation

| | |
|---|---|
| Example 3 | 40.00 mL |
| 1,3-butyleneglycol | 6.00 g |
| Concentrated glycerin | 6.00 g |
| Methylpolysiloxane | 6.00 g |
| Stearic acid | 3.00 g |
| Cetanol | 3.00 g |
| Cetyl 2-ethylhexanoate | 6.00 g |
| Squalene | 6.00 g |
| Sucrose fatty acid ester | 3.00 g |
| Natural vitamin E | 0.30 g |
| Sodium casein | 1.50 g |
| Disodium edetate | 0.03 g |
| Parabenzene | 0.30 g |

Brought to a final weight of 100.00 g by addition of purified water.

COMPARATIVE EXAMPLE 1

COMPARATIVE EXAMPLE 2

COMPARATIVE EXAMPLE 4

Cream Preparation

| | |
|---|---|
| 1,3-butyleneglycol | 6.00 g |
| Concentrated glycerin | 6.00 g |
| Methylpolysiloxane | 6.00 g |
| Stearic acid | 3.00 g |
| Cetanol | 3.00 g |
| Cetyl 2-ethylhexanoate | 6.00 g |
| Squalene | 6.00 g |
| Sucrose fatty acid ester | 3.00 g |
| Natural vitamin E | 0.30 g |
| Sodium casein | 1.50 g |
| Disodium edetate | 0.03 g |
| Parabenzene | 0.30 g |

Brought to a final weight of 100.00 g by addition of purified water.

Panelists: 4 healthy volunteers

Test Method: After inducing chapped skin by treating a healthy site of the skin for 30 minutes with 5% SDS, each sample was applied twice per day, and the instantaneous moisture retention ability before application and from 1 day to 2 weeks after application was measured according to the same method as Test Example 3.

Chapped Skin Induction Method: A glass cylinder was placed on the test site and fixed in position with tape. Next, 10 mL of 5% SDS (sodium lauryl sulfate) were poured into the glass cylinder to perform chapped skin treatment for 30 minutes while stirring occasionally. Finally, the SDS was suctioned out of the glass cylinder and the glass cylinder was removed.

Test Apparatus: Same as Test Example 2.

Figure 8:
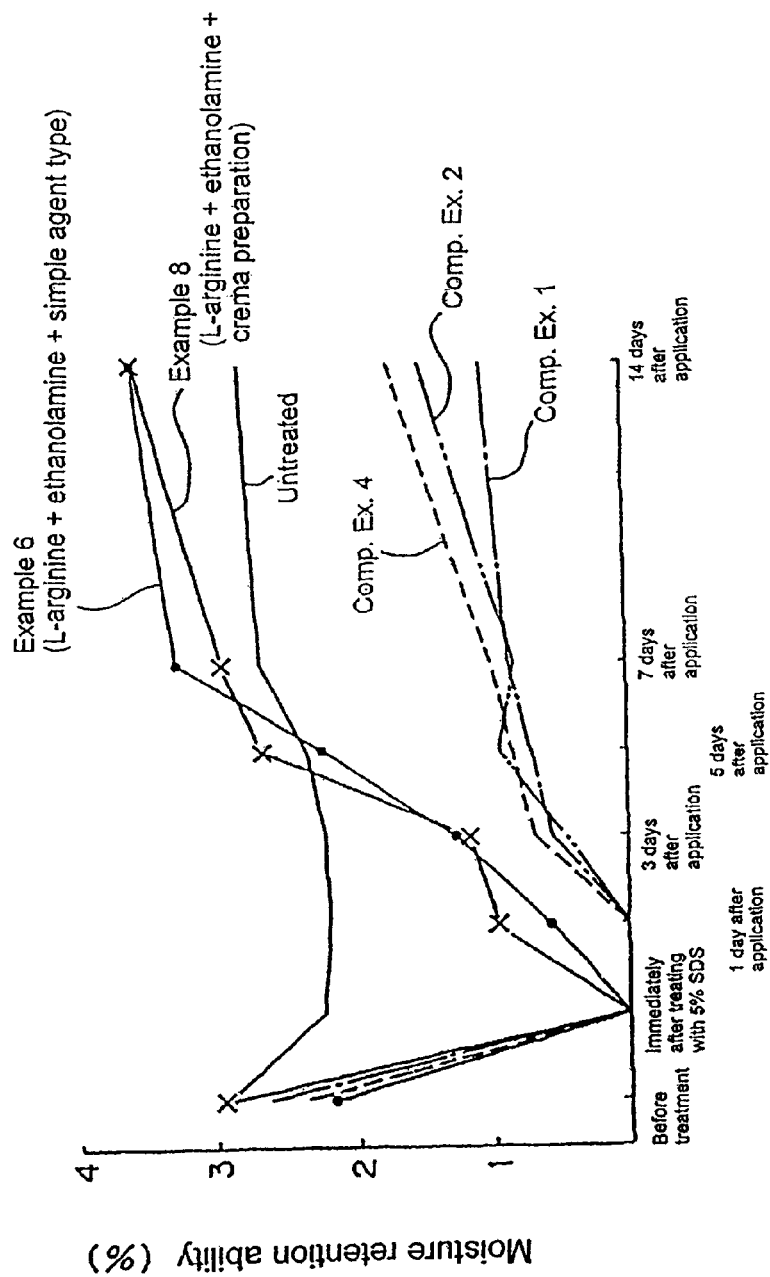
FIG. 8 shows the results of a chapped skin recovery test according to embodiments of the present invention.

Test Results:

According to the results of the chapped skin recovery test (FIG. 8), only natural recovery of the skin was observed with the simple preparation form, the typical moisture retention agent, hyaluronic acid, and a typical cream preparation not containing L-arginine or ethanolamine, and chapped skin improvement effects were not observed. On the other hand, in the case of Examples 6 and 8, moisture retention ability increased significantly in comparison with the control group at 3, 5 and 7 days after the start of application, and moisture retention ability was higher than the untreated site (healthy site) starting at 5 days after the start of application.

In this manner, Examples 6 and 8 were clearly demonstrated to rapidly restore damaged skin and improve the skin to healthy skin to a greater extent than the untreated site.

The present invention was proven to rapidly restore damaged skin in a short period of time, enable the skin to reach a state that is healthier than its original state, and have effects that improve the skin to its healthiest state. On the basis of these findings, the present invention was proven to act on chapped skin itself and condition it, be able to prevent skin diseases caused by chapped skin, and demonstrate chapped skin therapeutic effects.

TEST EXAMPLE 6

A clinical test was conducted on dry eczema, xeroderma and facial dry eczema patients to observe the therapeutic effects on skin diseases produced by skin conditioning, and those effects were evaluated in terms of the severity score of itchiness, induration, cornification, scaling, cracking, erythema, dryness and wrinkles, as well as overall improvement (usefulness) with respect to each disease.

Samples:

EXAMPLE 9

L-arginine+Milky Liquid Preparation

| | |
|---|---|
| L-arginine (Nakarai Tesk) | 0.10 g |
| 1,3-butyleneglycol | 10.00 g |
| Concentrated glycerin | 1.00 g |
| Stearic acid | 0.50 g |
| Myristic acid | 0.50 g |
| Bleached beeswax | 0.50 g |
| Tri-2-ethylhexanoate glycerin | 4.80 g |
| Octyldodecylmyristic acid | 2.00 g |
| Squalene | 1.00 g |
| Sucrose fatty acid ester | 0.60 g |
| Xanthane rubber | 0.10 g |
| Natural vitamin E | 0.10 g |
| Sodium casein | 0.30 g |
| Citric acid | As suitable |
| Disodium edetate | 0.02 g |
| Parabenzene | 0.20 g |

Brought to a final weight of 100.00 g by addition of soft water.

Panelists: 3 patients with dry eczema
2 patients with xeroderma
2 patients with facial dry eczema Test Sites:
Sites having symptoms suitable for evaluation and sites that can be compared to the left or right or above or below (comparison with non-application).

External Application Method: Simple application twice per day (morning and evening).

Application Period: 3 weeks

Figure 9:
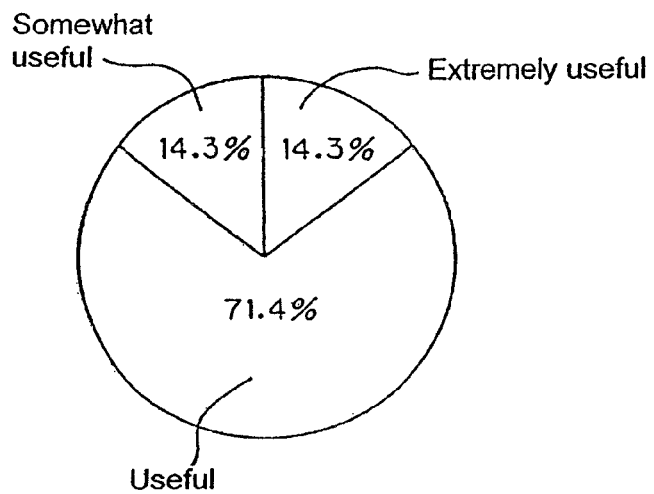
FIG. 9 shows the overall improvement (usefulness) of using embodiments of the present invention in dry eczema, xeroderma and facial dry eczema patients.

Evaluation Items:
Evaluation items consisted of:
(1) Itchiness
(2) Induration/cornification
(3) Scaling
(4) Cracking
(5) Erythema
(6) Dryness
(7) Wrinkles Evaluation Method:
The evaluation items were evaluated according to the following four levels of a severity score as determined by visual examination.
3: Advanced symptoms
2: Moderate symptoms
1: Mild symptoms
0: No symptoms or symptoms disappeared In addition, overall improvement (usefulness) was evaluated according to the following four levels:
Extremely useful
Useful
Somewhat useful
Not useful Test Results:
The results for overall improvement (usefulness) are as shown in FIG. 9. When Example 9 was used in patients with dry eczema, xeroderma and facial dry eczema, the results demonstrated overall improvement of 100%, a high degree of usefulness was obtained, and Example 9 was recognized to be extremely useful against these diseases.

Figure 10:
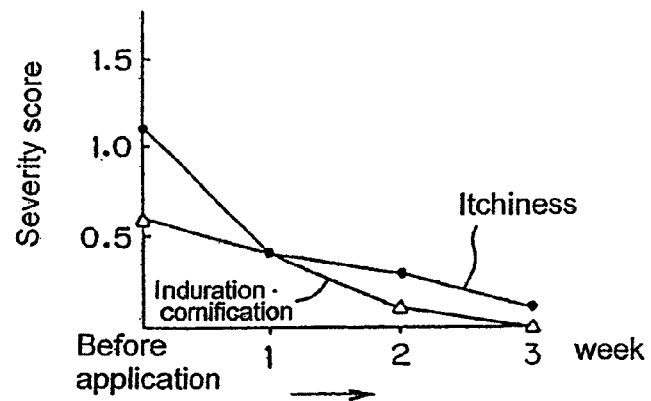
FIG. 10 shows improvement of itchiness, induration and cornification by embodiments of the present invention.
Figure 11:
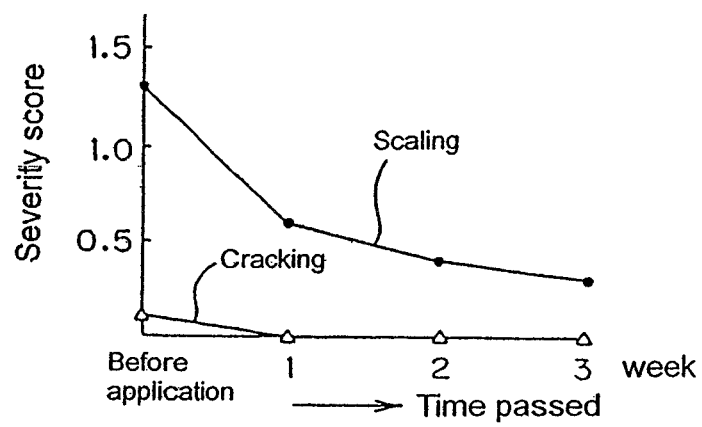
FIG. 11 shows improvement of scaling and cracking by embodiments of the present invention.
Figure 12:
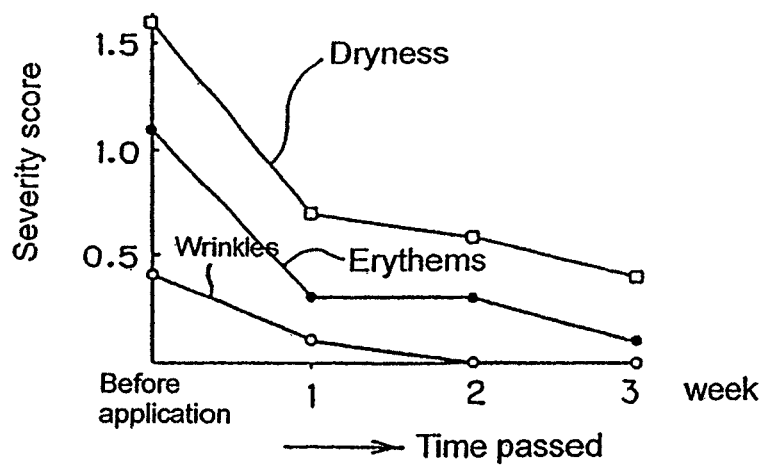
FIG. 12 shows improvement of erythema, dryness and wrinkles by embodiments of the present invention.

FIG. 10 shows the changes in severity scores for itchiness, induration and cornification. FIG. 11 shows the changes in severity scores for scaling and cracking. FIG. 12 shows the changes in severity scores for erythema, dryness and wrinkles. All effects appeared rapidly, and all symptoms were alleviated considerably after 1 week of use. Favorable improvement effects were also observed after 1 week, and nearly all symptoms had either been alleviated or disappeared after 3 weeks. Furthermore, there were no adverse side effects observed at all, there were no cases of relapse after use was discontinued, and the patients were completely healed.

In this manner, the present invention is able to improve symptoms observed in skin diseases such as itchiness, induration, cornification, scaling, cracking, erythema, dryness and wrinkles through conditioning of the skin.

TEST EXAMPLE 7

A clinical test was conducted on asteatosis, xeroderma, facial dry eczema and progressive volar keratoderma patients to observe the therapeutic effects on skin diseases produced by skin conditioning, and those effects were evaluated in terms of the severity score of itchiness, induration, cornification, scaling, cracking, erythema, dryness and wrinkles, as well as overall improvement (usefulness) with respect to each disease.

Samples:

EXAMPLE 10

L-arginine+Ethanolamine+Milky Liquid Preparation

| | |
|---|---|
| Example 3 | 35.00 mL |
| 1,3-butyleneglycol | 10.00 g |

-continued

| | | |
|---|---|---|
| Concentrated glycerin | 1.00 g | |
| Stearic acid | 0.50 g | |
| Myristic acid | 0.50 g | |
| Bleached beeswax | 0.50 g | |
| Tri-2-ethylhexanoate glycerin | 4.80 g | |
| Octyldodecylmyristic acid | 2.00 g | |
| Squalene | 1.00 g | |
| Sucrose fatty acid ester | 0.60 g | |
| Xanthane rubber | 0.10 g | |
| Natural vitamin E | 0.10 g | |
| Sodium casein | 0.30 g | |
| Citric acid | As suitable | |
| Disodium edetate | 0.02 g | |
| Parabenzene | 0.20 g | |

Brought to a final weight of 100.00 g by addition of soft water.

| | | |
|---|---|---|
| Panelists: | Asteatosis patients | 6 |
| | Xeroderma patients | 4 |
| | Facial dry eczema patients | 4 |
| | Progressive volar keratoderma patients | 5 |

Test Sites:
Sites having symptoms suitable for evaluation and sites that can be compared to the left or right or above or below (comparison with non-application).

External Application Method: Simple application twice per day (morning and evening).

Figure 13:
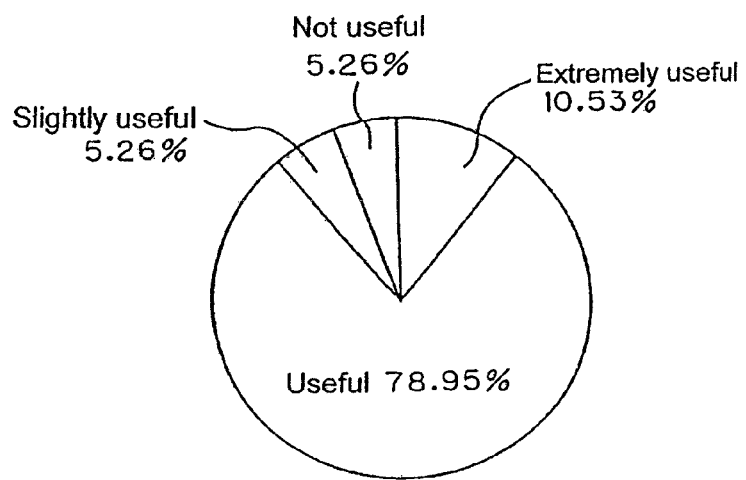
FIG. 13 shows overall improvement (usefulness) of using embodiments of the present invention in asteatosis, xeroderma, facial dry eczema and progressive volar keratoderma patients.

Application Period: 3 weeks
Evaluation Items:
Evaluation items consisted of:
(1) Itchiness
(2) Induration/cornification
(3) Scaling
(4) Cracking
(5) Erythema
(6) Dryness
(7) Wrinkles Evaluation Method:
The evaluation items were evaluated according to the following four levels of a severity score as determined by visual examination.
3: Advanced symptoms
2: Moderate symptoms
1: Mild symptoms
0: No symptoms or symptoms disappeared In addition, overall improvement (usefulness) was evaluated according to the following four levels:
Extremely useful
Useful
Somewhat useful
Not useful Test Results:
Overall improvement (usefulness) was as shown in FIG. 13.

When Example 10 was used in asteatosis, xeroderma, facial dry eczema and progressive volar keratoderma patients, it demonstrated overall improvement of 94.74%, a high degree of usefulness was obtained, and Example 10 was observed to be extremely useful against these diseases.

Figure 14:
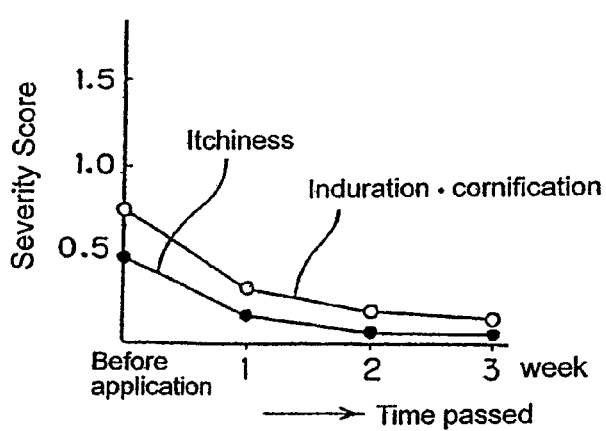
FIG. 14 shows improvement of itchiness, induration and cornification by embodiments of the present invention.
Figure 15:
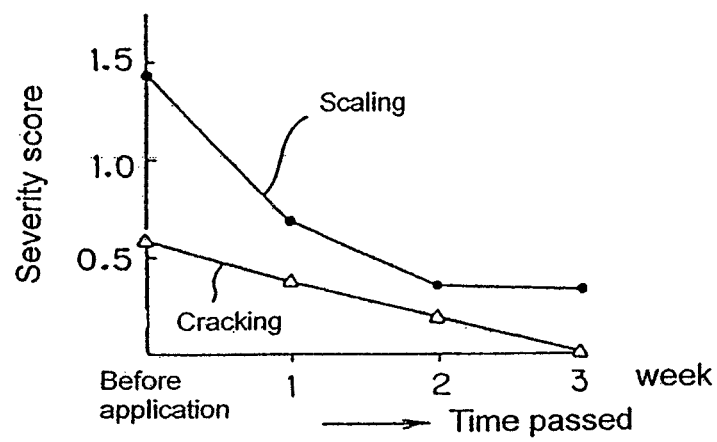
FIG. 15 shows improvement of scaling and cracking by embodiments of the present invention.
Figure 16:
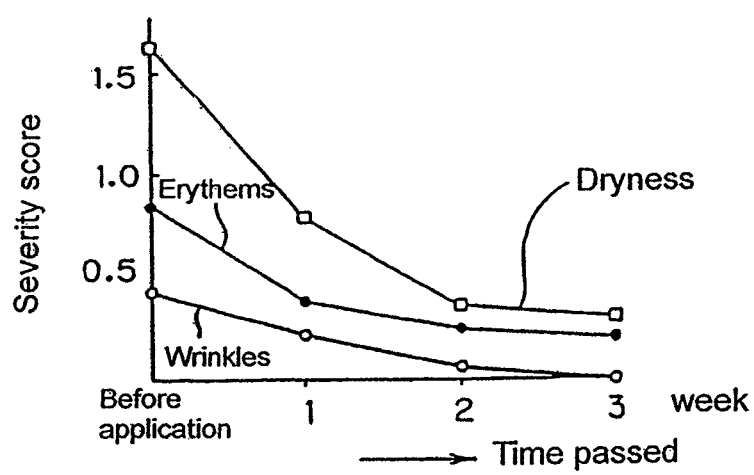
FIG. 16 shows improvement of erythema, dryness and wrinkles by embodiments of the present invention.
Figure 17:
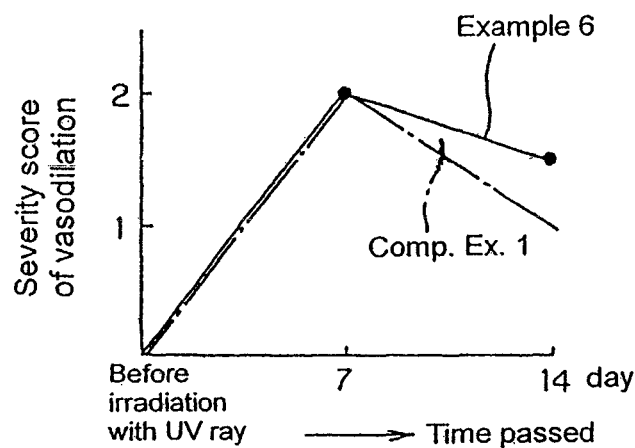
FIG. 17 shows changes in the severity score of vasodilation by embodiments of the present invention.
Figure 18:
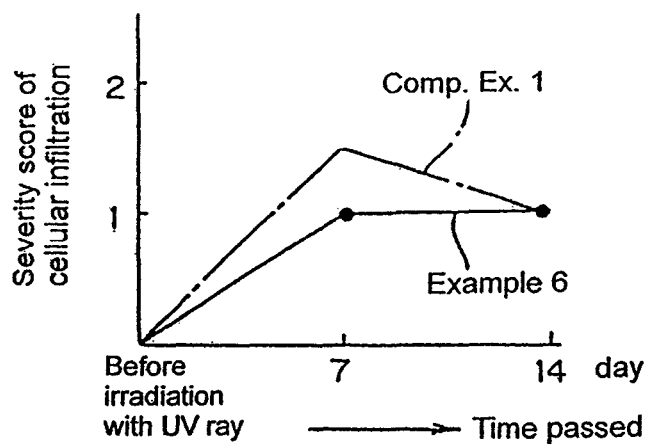
FIG. 18 shows changes in the severity score of cellular infiltration by embodiments of the present invention.
Figure 19:
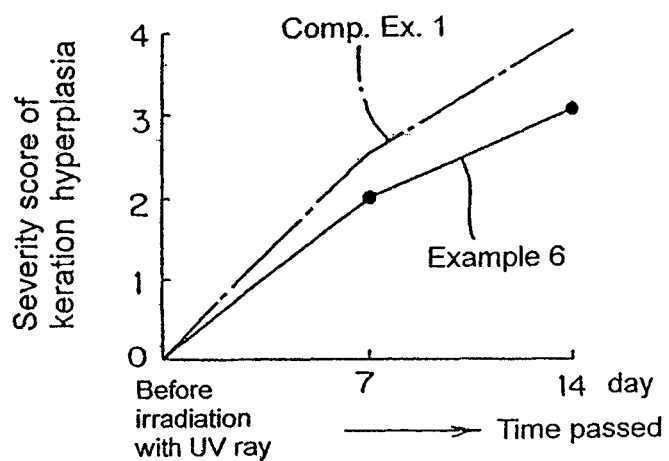
FIG. 19 shows changes in the severity score of keratin hyperplasia by embodiments of the present invention.
Figure 20:
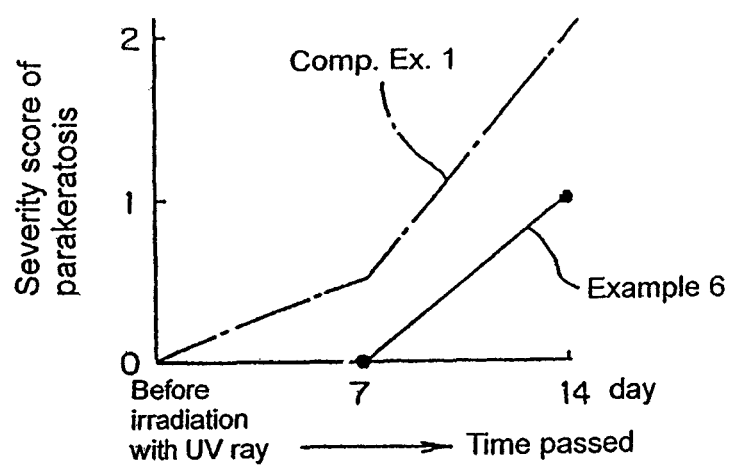
FIG. 20 shows changes in the severity score of parakeratosis by embodiments of the present invention.
Figure 21:
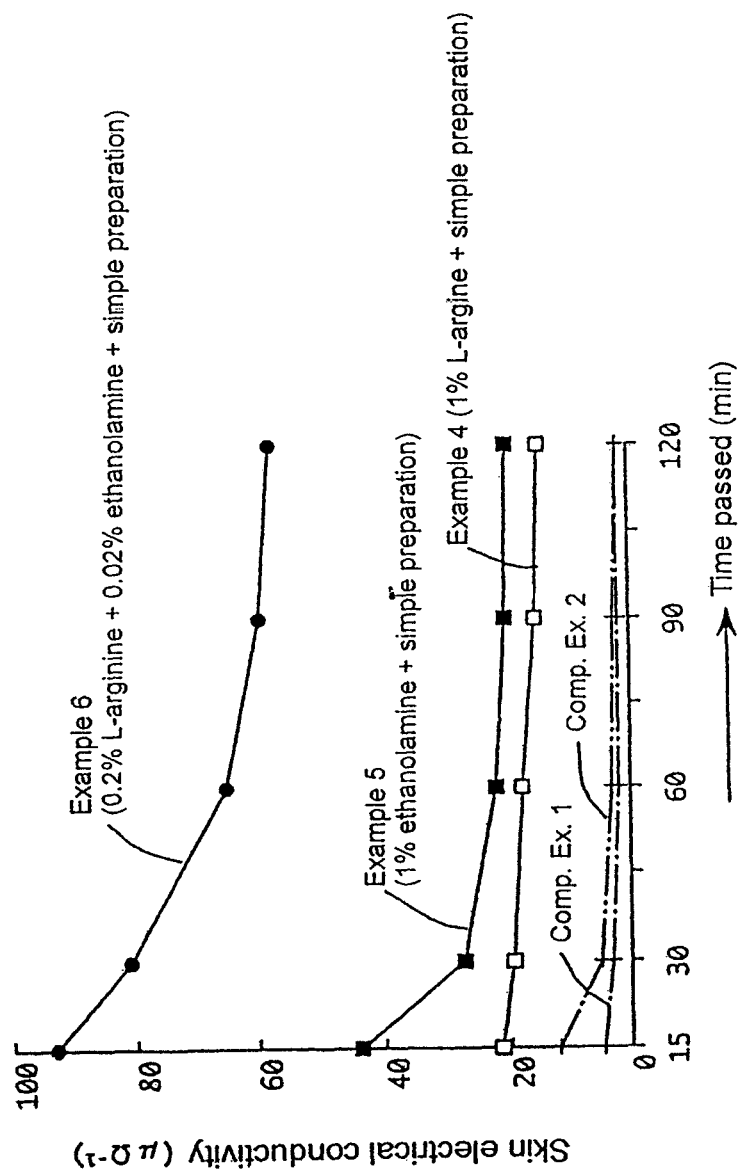
FIGS. 21 to 31 show the results of a moisture retention duration test performed on atopic skin according to embodiments of the present invention.
Figure 22:
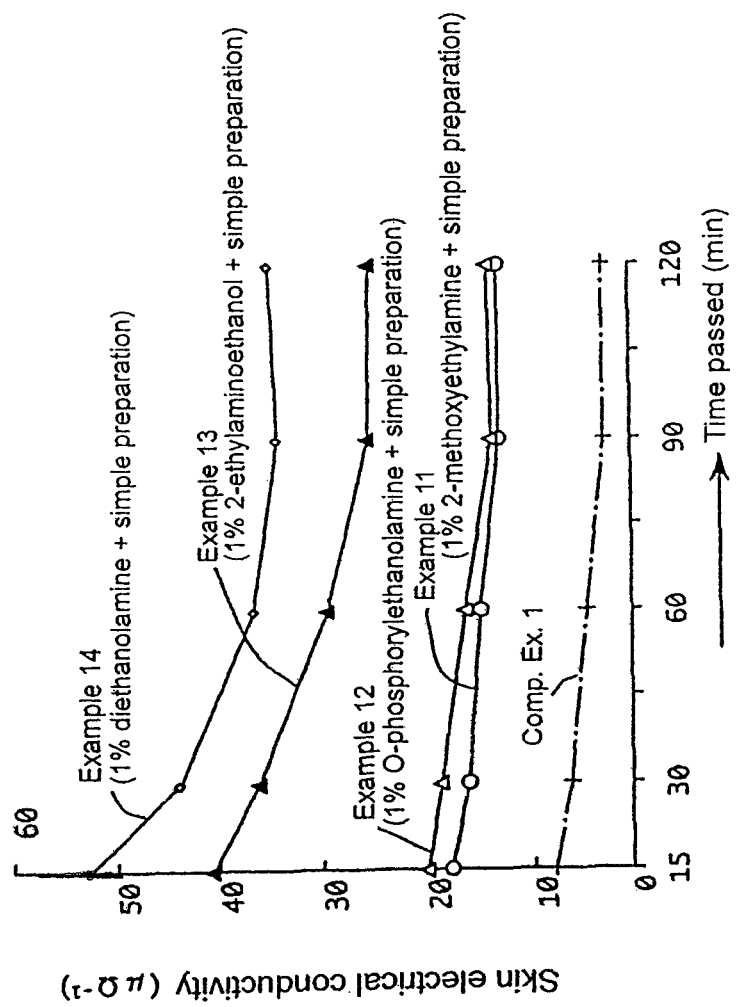
Figure 23:
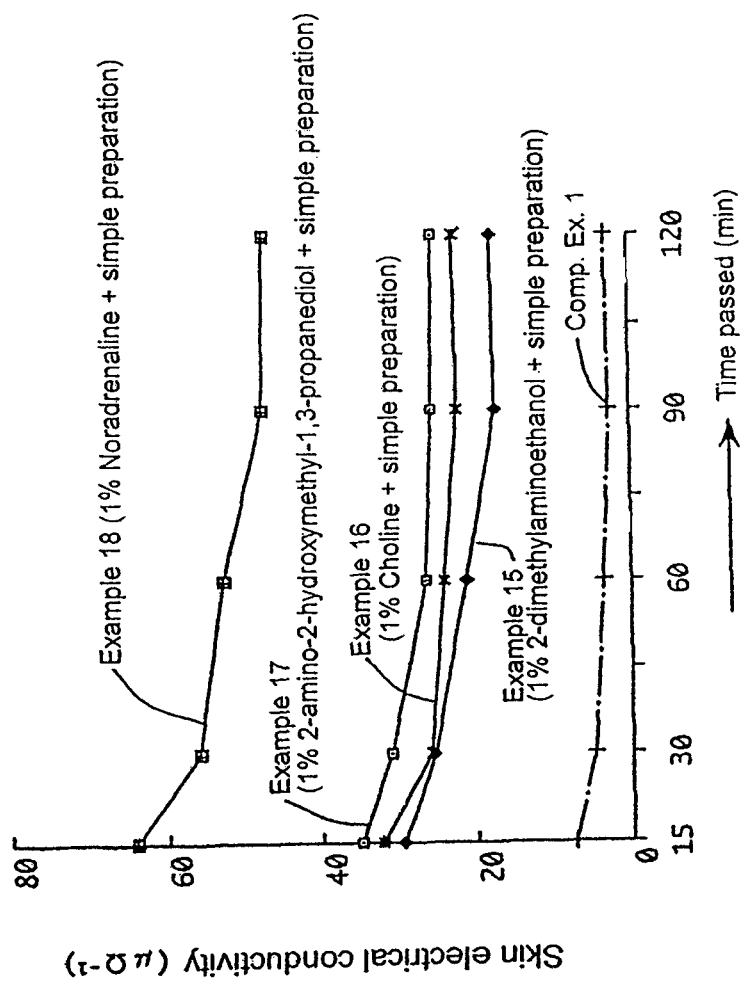
Figure 24:
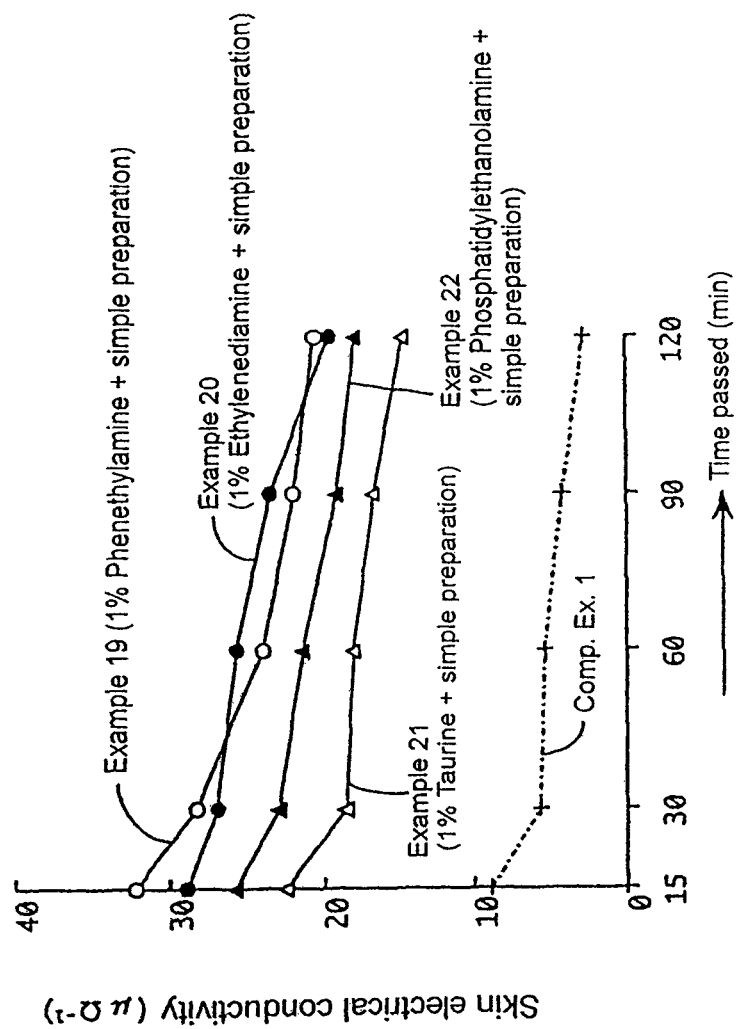
Figure 25:
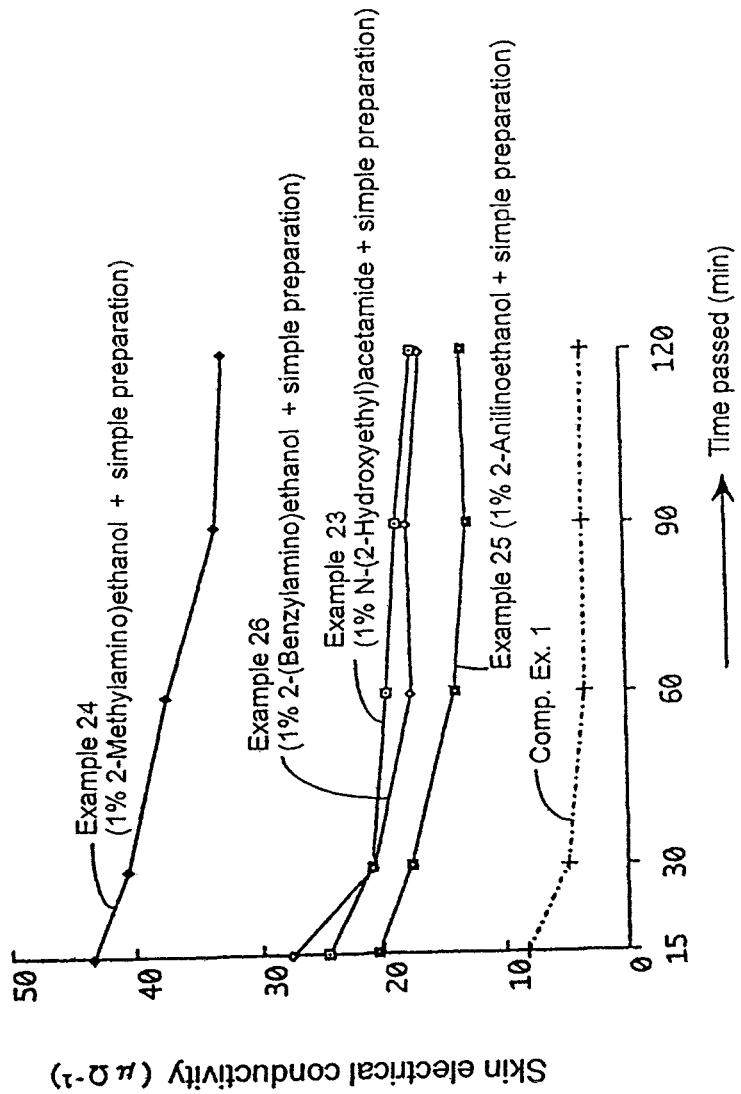
Figure 26:
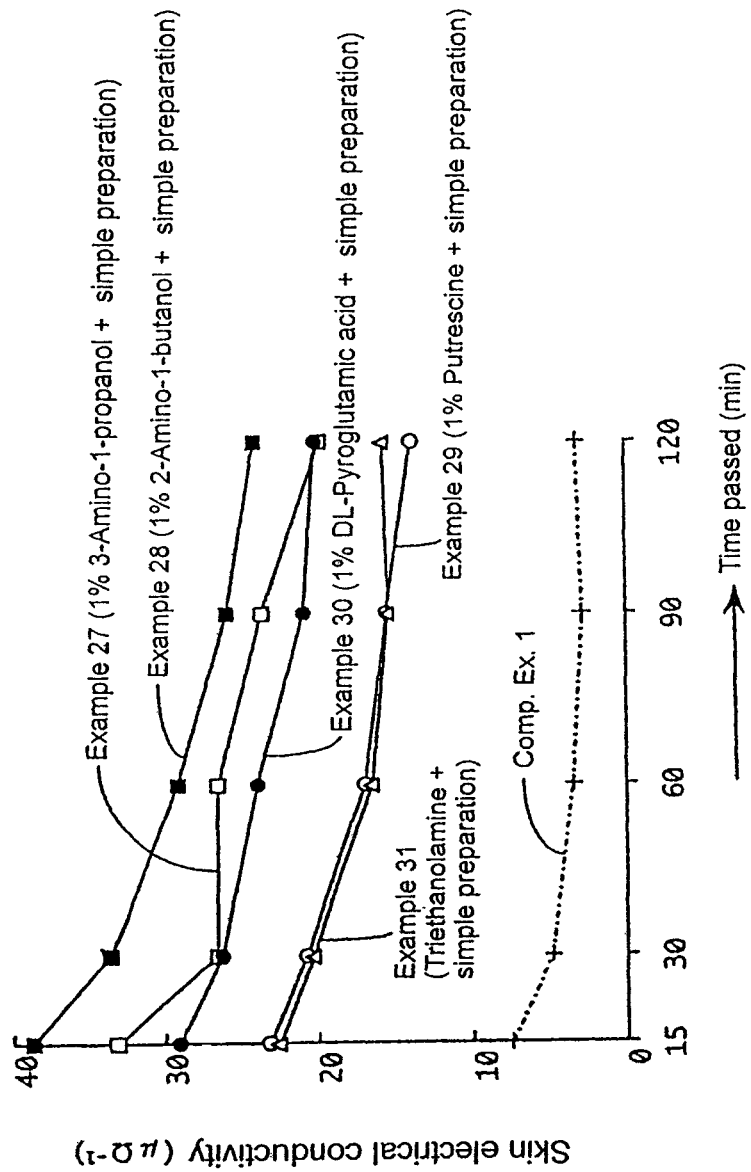
Figure 27:
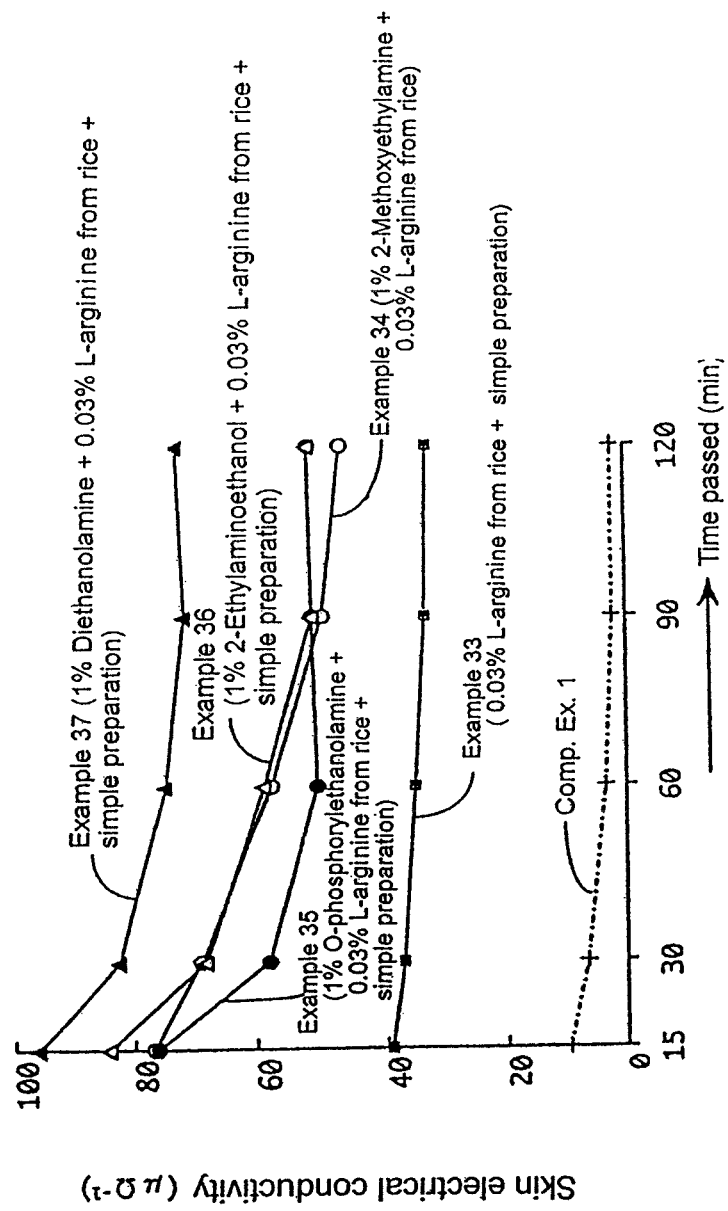
Figure 28:
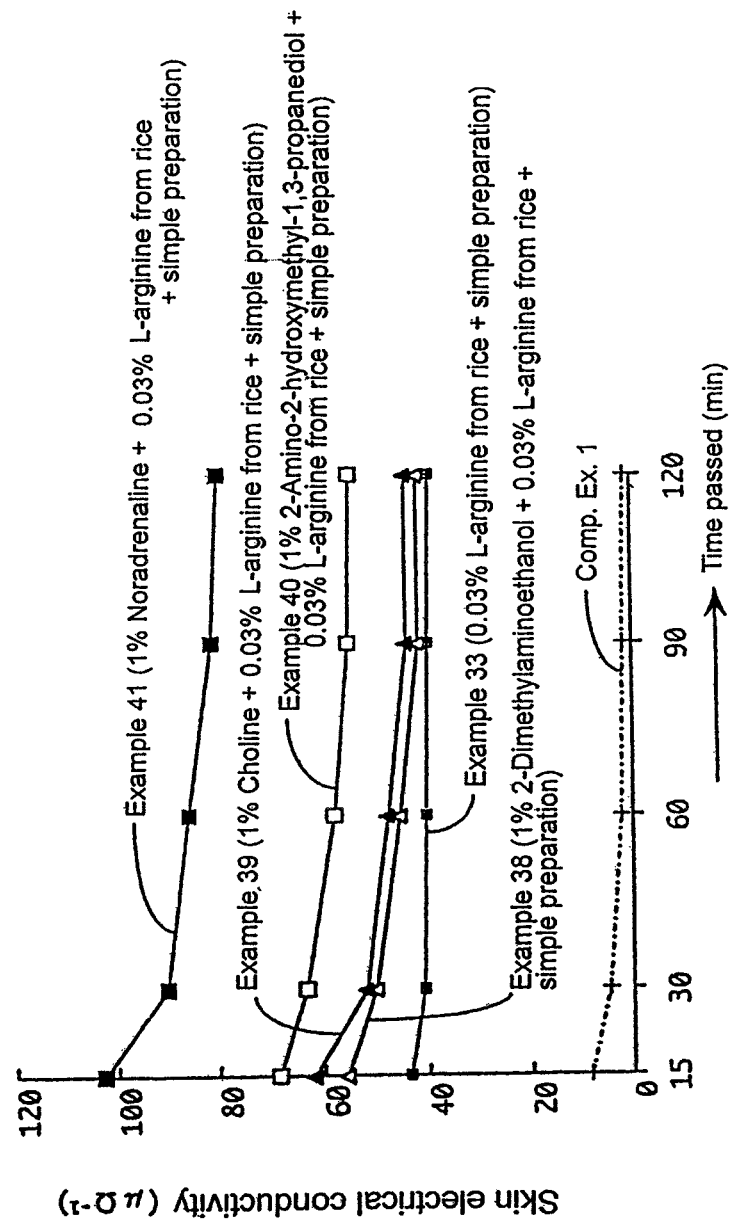
Figure 29:
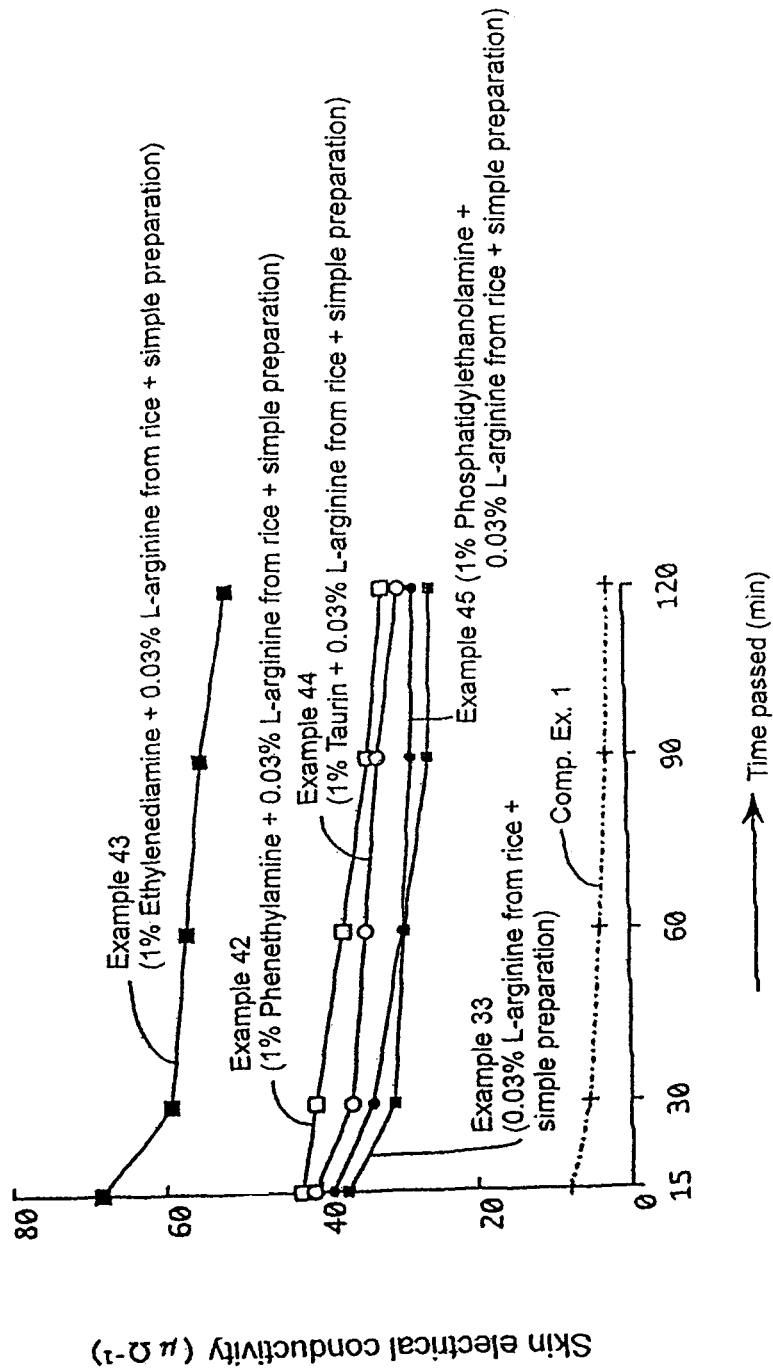
Figure 30:
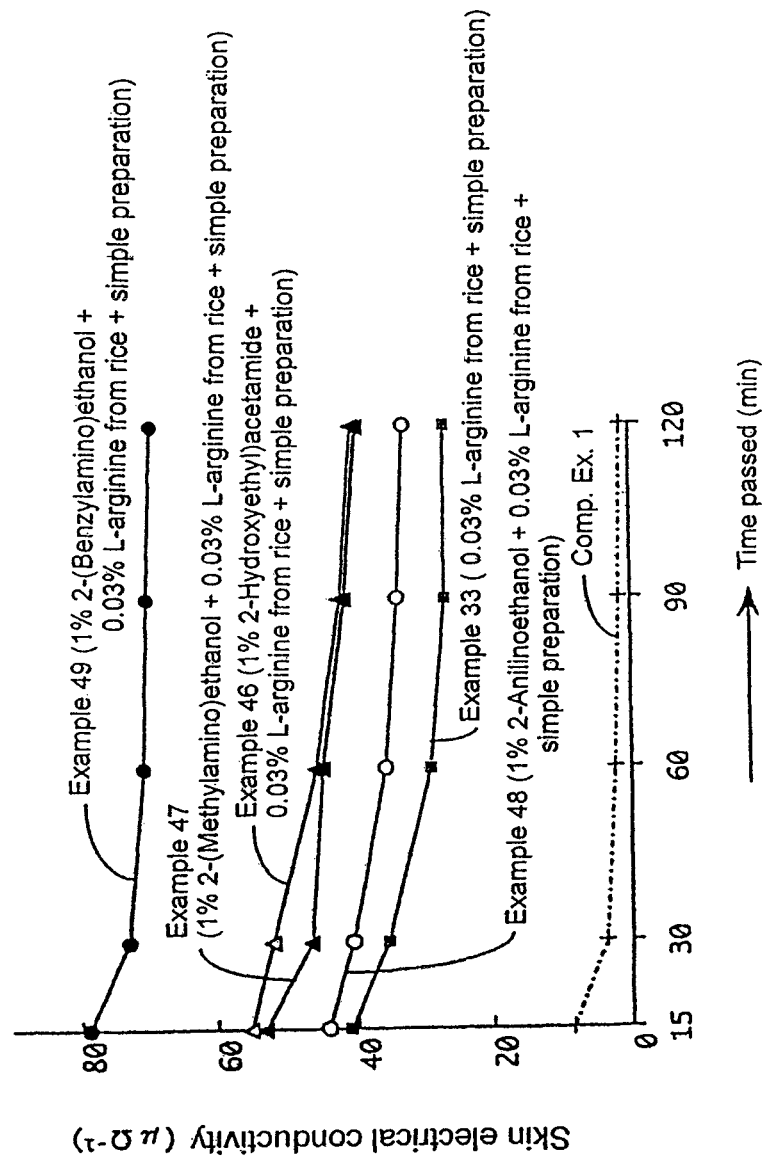
Figure 31:
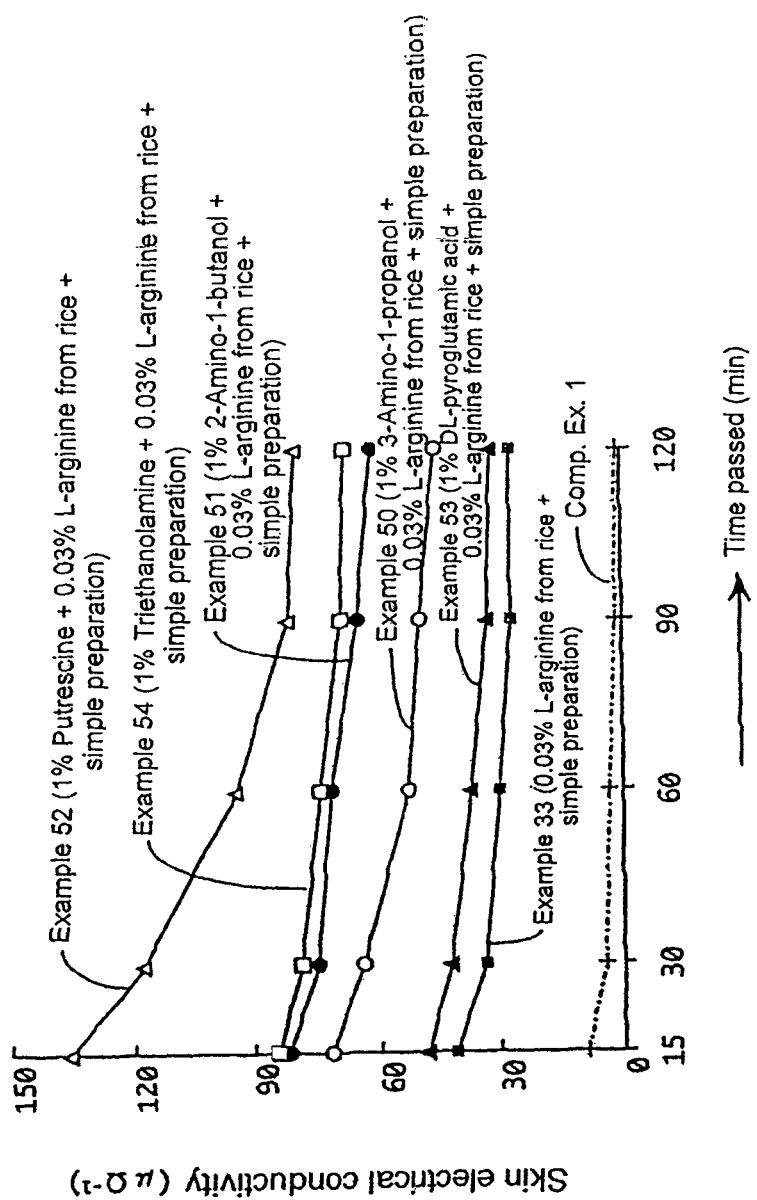

FIG. 14 shows the changes in severity scores for itchiness, induration and cornification, FIG. 15 shows the changes in severity scores for scaling and cracking, and FIG. 16 shows the changes in severity scores for erythema, dryness and wrinkles. All effects appeared rapidly, and all symptoms were alleviated considerably after 1 week of use. Favorable improvement effects were also observed after 1 week, and nearly all symptoms had either been alleviated or disappeared after 3 weeks. Furthermore, there were no adverse side effects observed at all, there were no cases of relapse after use was discontinued, and the patients were completely healed.

In this manner, the present invention is able to improve symptoms observed in skin diseases such as itchiness, induration, cornification, scaling, cracking, erythema, dryness and wrinkles through conditioning of the skin.

TEST EXAMPLE 8

Guinea pigs were irradiated with ultraviolet light, a phlogogenic factor, followed by histological examination of the degree of inflammatory changes in epidermal tissue and dermal tissue to observe the preventive and therapeutic effects on inflammation and photoinflammation.

Samples:

EXAMPLE 6

L-arginine+Ethanolamine+Simple Preparation

COMPARATIVE EXAMPLE 1

Simple Preparation

Experimental Animals: Guinea pigs, 5
Test Site:
Shaved back of guinea pigs (comparison with simple preparation)

Test Method:
The backs of the experimental animals were shaved and hair was removed with a depilatory cream three days before irradiation with ultraviolet light.

The test site was irradiated with ultraviolet light, and application of samples was started immediately after irradiation.

In order to make a histological evaluation of inflammation caused by irradiation with ultraviolet light, biopsies were performed with a 6 mm disposable punch on days 7 and 14 after irradiation, the specimens were immersed in 10% neutral formalin solution and fixed followed by preparing tissue sections.

Application Method: Simple application twice a day after irradiation (morning and evening)
Application Period: 2 weeks Evaluation Method:
Using keratin hyperplasia and parakeratosis as indicators of inflammatory changes of epidermal tissue, and cellular infiltration and vasodilation as indicators of inflammatory changes in dermal tissue, the tissue sections were observed and evaluations were made according to the following five levels of a severity score (inflammation intensity).

Severity Score
4: Advanced symptoms
3: Moderate symptoms
2: Mild symptoms
1: Slight symptoms
0: No symptoms or symptoms disappeared Test Results:
The test results are as shown in FIGS. 17, 18, 19 and 20.

Example 6 of the present invention was clearly demonstrated to have an effect that heals vasodilation in the early stage of the occurrence of inflammation in dermal tissue, and was also observed to not only have a therapeutic effect in the early stage, but also a preventive effect that prevents full-scale onset of inflammation. In addition, it was also clearly shown to rapidly heal cellular infiltration, which is a symptom of inflammation in the dermis. Furthermore, keratin hyperplasia and parakeratosis, which are abnormalities in the epidermis accompanying inflammation, were also observed to be alleviated.

On the basis of these findings, inflammation and photoinflammation were clearly demonstrated to be prevented and healed by skin conditioning.

TEST EXAMPLE 9

A 2-hour moisture retention duration test was performed on atopic skin.

Panelists: 7 persons with atopic skin
Test Method: Same as Test Example 2
Measurement Method: Same as Text Example 2
Test Apparatus: Same as Test Example 2
The samples were as shown below.

EXAMPLE 4

1% L-arginine Simple Preparation

| L-arginine (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 5

1% Ethanolamine Simple Preparation

| Ethanolamine (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 6

0.2% L-arginine+0.02% Ethanolamine+Simple Preparation

| Example 3 | 90.00 mL |
| 95% ethanol | 2.00 mL |
| Parabenzene | 0.18 g |
| Purified soy bean lecithin | 0.05 g |

Brought to a final weight of 100.00 g by addition of purified water.

EXAMPLE 11

1% 2-methoxyethylamine Simple Preparation

| 2-methoxyethylamine (Toko Kasei Kogyo., Ltd.) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 12

1% O-phosphorylethanolamine Simple Preparation

| O-phosphorylethanolamine (Toko Kasei Kogyo., Ltd) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 13

1% 2-ethylaminoethanol Simple Preparation

| 2-ethylaminoethanol (Tokyo Kasei Kogyo Co., Ltd) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 14

1% diethanolamine Simple Preparation

| Diethanolamine (Mitsui Toatsu Chemicals Inc.) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 15

1% 2-dimethylaminoethanol Simple Preparation

| 2-dimethylaminoethanol (Kanto Kagaku) | 1.00 g |
| 95% ethanol | 2.00 mL |

EXAMPLE 16

1% Choline Simple Preparation

| | |
|---|---|
| Choline (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 17

1% 2-amino-2-hydroxymethyl-1,3-propanediol Simple Preparation

| | |
|---|---|
| 1% 2-amino-2-hydroxymethyl-1,3-propanediol (Kanto Kogyo) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 18

1% Noradrenaline Simple Preparation

| | |
|---|---|
| Noradrenaline (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 19

1% Phenethylamine Simple Preparation

| | |
|---|---|
| Phenethylamine (Kanto Kagaku) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 20

1% Ethylenediamine Simple Preparation

| | |
|---|---|
| Ethylenediamine (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 21

1% Taurine Simple Preparation

| | |
|---|---|
| Taurine (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 22

1% Phosphatidylethanolamine Simple Preparation

| | |
|---|---|
| Phosphatidylethanolamine (Kanto Kagaku) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 23

1% N-2-hydroxyethyl)acetamido Simple Preparation

| | |
|---|---|
| N-2-hydroxyethyl)acetamido (Kanto Kagaku) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 24

1% 2-methylamino)ethanol Simple Preparation

| | |
|---|---|
| 2-methylamino)ethanol (Kanto Kagaku) | 1.00 g |
| 95% ethanol | 2.00 mL |

-continued

| | |
|---|---|
| Parabenzene | 0.18 g |
| Purified soy bean lecithin | 0.05 g |

Brought to a final weight of 100.00 g by addition of purified water.

EXAMPLE 25

1% 2-anilinoethanol Simple Preparation

| | |
|---|---|
| 2-anilinoethanol (Kanto Kagaku) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 26

1% 2-benzylamino)ethanol Simple Preparation

| | |
|---|---|
| 2-benzylamino)ethanol (Kanto Kagaku) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 27

1% 3-amino-1-propanol Simple Preparation

| | |
|---|---|
| 3-amino-1-propanol (Kanto Kagaku) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 28

1% 2-amino-1-butanol Simple Preparation

| | |
|---|---|
| 2-amino-1-butanol (Nakarai Tesk) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 29

1% putrescine Simple Preparation

| | |
|---|---|
| Putrescine (Sigma Chemical) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 30

1% DL-pyroglutamic Acid Simple Preparation

| | |
|---|---|
| DL-pyroglutamic acid (Tokyo Kasei Kogyo Co., Ltd.) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 31

1% Triethanolamine Simple Preparation

| | |
|---|---|
| Triethanolamine (Mitsui Toatsu Chemicals Inc.) | 1.00 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 32

Rice Preparation Containing 0.03% L-arginine 1 kg of unpolished rice was crushed with a crusher. After adding 3000 mL of water, 7.5 g of α-amylase, 8 g of protease and 8 g of peptidase and heating to 55° C., the mixture was allowed to stand for 10 hours while holding at that temperature. Next, the temperature was gradually raised and extraction was performed by boiling for 5 minutes. After cooling to 20° C., the mixture was press-filtered and the pH of the filtrate was lowered to 3.3 by addition of citric acid. 8 g of acidic protease and 8 g of acidic carboxypeptidase were added followed by allowing to react for 10 hours at 55° C.

Next, the mixture was heated to 70° C. and then filtered after cooling to obtain 2700 mL of product containing 354 mg/L of L-arginine.

EXAMPLE 33

Rice Preparation Containing 0.03% L-arginine+Simple Preparation

| | |
|---|---|
| Example 32 (containing 0.03% L-arginine from rice) | 90.00 mL |
| 95% ethanol | 2.00 mL |
| Parabenzene | 0.18 g |
| Purified soy bean lecithin | 0.05 g |

Brought to a final weight of 100.00 g by addition of purified water.

EXAMPLE 34

1% 2-methoxyethylamine+Rice Preparation Containing 0.03% L-arginine+Simple Preparation

| | |
|---|---|
| Example 32 (containing 0.03% L-arginine from rice) | 90.00 mL |
| 2-methoxyethylamine (Tokyo Kasei Kogyo Co., Ltd.) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 35

1% O-phosphorylethanolamine+Rice Preparation Containing 0.03% L-arginine+Simple Preparation

| | |
|---|---|
| Example 32 (containing 0.03% L-arginine from rice) | 90.00 mL |
| O-phosphorylethanolamine (Tokyo Kasei Kogyo Co., Ltd.) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 36

1% 2-ethtylaminoethanol+Rice Preparation Containing 0.03% L-arginine+Simple Preparation

| | |
|---|---|
| Example 32 (containing 0.03% L-arginine from rice) | 90.00 mL |
| 2-ethtylaminoethanol | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 37

1% Diethanolamine+Rice Preparation Containing 0.03% L-arginine+Simple Preparation

| | |
|---|---|
| Example 32 (containing 0.03% L-arginine from rice) | 90.00 mL |
| Diethanolamine | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 38

1% 2-dimethylaminoethanol+Rice Preparation Containing 0.03% L-arginine+Simple Preparation

| | |
|---|---|
| Example 32 (containing 0.03% L-arginine from rice) | 90.00 mL |
| 2-dimethylaminoethanol (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 39

1% Choline+Rice Preparation Containing 0.03% L-arginine+Simple Preparation

| | |
|---|---|
| Example 32 (containing 0.03% L-arginine from rice) | 90.00 mL |
| Choline (Nakarai Tesk) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 40

1% 2-amino-2-hydroxymethyl-1,3-propanediol+Rice Preparation Containing 0.03% L-arginine+Simple Preparation

| | |
|---|---|
| Example 32 (containing 0.03% L-arginine from rice) | 90.00 mL |
| 2-amino-2-hydroxymethyl-1,3-propanediol (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 41

1% Noradrenaline+Rice Preparation Containing 0.03% L-arginine+Simple Preparation

| | |
|---|---|
| Example 32 (containing 0.03% L-arginine from rice) | 90.00 mL |
| Noradrenaline (Nakarai Tesk) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 42

1% Phenethylamine+Rice Preparation Containing 0.03% L-arginine+Simple Preparation

| | |
|---|---|
| Example 32 (containing 0.03% L-arginine from rice) | 90.00 mL |
| Phenethylamine (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 43

1% Ethylenediamine+Rice Preparation Containing 0.03% L-arginine+Simple Preparation

| | |
|---|---|
| Example 32 (containing 0.03% L-arginine from rice) | 90.00 mL |
| Ethylenediamine (Nakarai Tesk) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 44

1% Taurine+Rice Preparation Containing 0.03% L-arginine+Simple Preparation

| | |
|---|---|
| Example 32 (containing 0.03% L-arginine from rice) | 90.00 mL |
| Taurine (Nakarai Tesk) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 45

1% Phosphatidylethanolamine+Rice Preparation Containing 0.03% L-arginine+Simple Preparation

| | |
|---|---|
| Example 32 (containing 0.03% L-arginine from rice) | 90.00 mL |
| Phosphatidylethanolamine (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 46

1% N-2-hydroxyethyl)acetamido+Rice Preparation Containing 0.03% L-arginine+Simple Preparation

| | |
|---|---|
| Example 32 (containing 0.03% L-arginine from rice) | 90.00 mL |
| N-2-hydroxyethyl)acetamido (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 47

1% 2-methylamino)ethanol+Rice Preparation Containing 0.03% L-arginine+Simple Preparation

| | |
|---|---|
| Example 32 (containing 0.03% L-arginine from rice) | 90.00 mL |
| 2-methylamino)ethanol (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 48

1% 2-anilinoethanol+Rice Preparation Containing 0.03% L-arginine+Simple Preparation

| | |
|---|---|
| Example 32 (containing 0.03% L-arginine from rice) | 90.00 mL |
| 2-anilinoethanol (Kanto Kagaku) | 0.90 g |
| 95% ethanol | 2.00 mL |
| Parabenzene | 0.18 g |
| Purified soy bean lecithin | 0.05 g |

EXAMPLE 49

1% 2-benzylamino)ethanol+Rice Preparation Containing 0.03% L-arginine+Simple Preparation

| | |
|---|---|
| Example 32 (containing 0.03% L-arginine from rice) | 90.00 mL |
| 2-(benzylamino)ethanol (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 50

1% 3-amino-1-propanol+Rice Preparation Containing 0.03% L-arginine+Simple Preparation

| | |
|---|---|
| Example 32 (containing 0.03% L-arginine from rice) | 90.00 mL |
| 3-amino-1-propanol (Kanto Kagaku) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 51

1% 2-amino-1-butanol+Rice Preparation Containing 0.03% L-arginine+Simple Preparation

| | |
|---|---|
| Example 32 (containing 0.03% L-arginine from rice) | 90.00 mL |
| 2-amino-1-butanol (Nakarai Tesk) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 52

1% Putrescine+Rice Preparation Containing 0.03% L-arginine+Simple Preparation

| | |
|---|---|
| Example 32 (containing 0.03% L-arginine from rice) | 90.00 mL |
| Putrescine (Sigma Chemical) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 53

1% DL-pyroglutamine Acid+Rice Preparation Containing 0.03% L-arginine+Simple Preparation

| | |
|---|---|
| Example 32 (containing 0.03% L-arginine from rice) | 90.00 mL |
| DL-pyroglutamine acid (Tokyo Kasei Kogyo Co., Ltd.) | 0.90 g |
| 95% ethanol | 2.00 mL |
| Parabenzene | 0.18 g |
| Purified soy bean lecithin | 0.05 g |

Brought to a final weight of 100.00 g by addition of purified water.

EXAMPLE 54

1% Triethanolamine+Rice Preparation Containing 0.03% L-arginine+Simple Preparation

| | |
|---|---|
| Example 32 (containing 0.03% L-arginine from rice) | 90.00 mL |
| Triethanolamine (Mitsui Toatsu Chemicals Inc.) | 0.90 g |
| 95% ethanol | 2.00 mL |
| Parabenzene | 0.18 g |
| Purified soy bean lecithin | 0.05 g |

Brought to a final weight of 100.00 g by addition of purified water.

COMPARATIVE EXAMPLE 1

Simple Preparation

| | |
|---|---|
| 95% ethanol | 2.00 mL |
| Parabenzene | 0.18 g |
| Purified soy bean lecithin | 0.05 g |

Brought to a final weight of 100.00 g by addition of purified water.

COMPARATIVE EXAMPLE 2

Hyaluronic Acid+Simple Preparation

| | |
|---|---|
| Sodium hyaluronate | 1.00 g |
| 95% ethanol | 2.00 mL |
| Parabenzene | 0.18 g |
| Purified soy bean lecithin | 0.05 g |

Brought to a final weight of 100.00 g by addition of purified water.

The results of the moisture retention duration test are as shown in FIGS. 21 through 31. With respect to atopic skin, moisture retention effects were remarkable 15 minutes after application, and moisture retention continued beyond 30 minutes for 2 hours. Although continuation of moisture retention was observed with either L-arginine or ethanolamine alone, when two types of substances were present, moisture retention duration was enhanced more than when either substance was used alone even at lower concentrations (see Example 6 in FIG. 21).

Although Examples 34 through 54 (referred to as the "former") are mixtures containing 0.03% L-arginine in Examples 11 through 31 (referred to as the "latter"), respectively, the former demonstrated higher moisture retention duration than the latter (see FIGS. 27 through 31).

TEST EXAMPLE 10

A moisture retention ability test was performed on atopic skin.

Panelists: 4 persons with atopic skin
Measurement Method: Same as measurement method of Test Example 3
Test Apparatus: Same as test apparatus of Test Example 2
The samples were as shown below.
Example 4 (1% L-arginine simple preparation)
Example 5 (1% ethanolamine simple preparation)
Example 6 (0.2% L-arginine+0.02% ethanolamine+simple preparation)
Example 11 (1% 2-methoxyethylamine+simple preparation)
Example 14 (1% diethanolamine simple preparation)
Example 16 (1% choline simple preparation)
Example 17 (1% 2-amino-2-hydroxymethyl-1,3-propanediol simple preparation)
Example 18 (1% noradrenalin simple preparation)
Example 34 (2-methoxyethylamine+rice preparation containing 0.03% L-arginine+simple preparation)
Example 37 (1% diethanolamine+rice preparation containing 0.03% L-arginine+simple preparation)
Example 39 (1% choline+rice preparation containing 0.03% L-arginine+simple preparation)
Example 40 (1% 2-amino-2-hydroxymethyl-1,3-propanediol+rice preparation containing 0.03% L-arginine+simple preparation)
Example 41 (1% noradrenalin+rice preparation containing 0.03% L-arginine+simple preparation)

COMPARATIVE EXAMPLE 1

Simple Preparation

Figure 32:
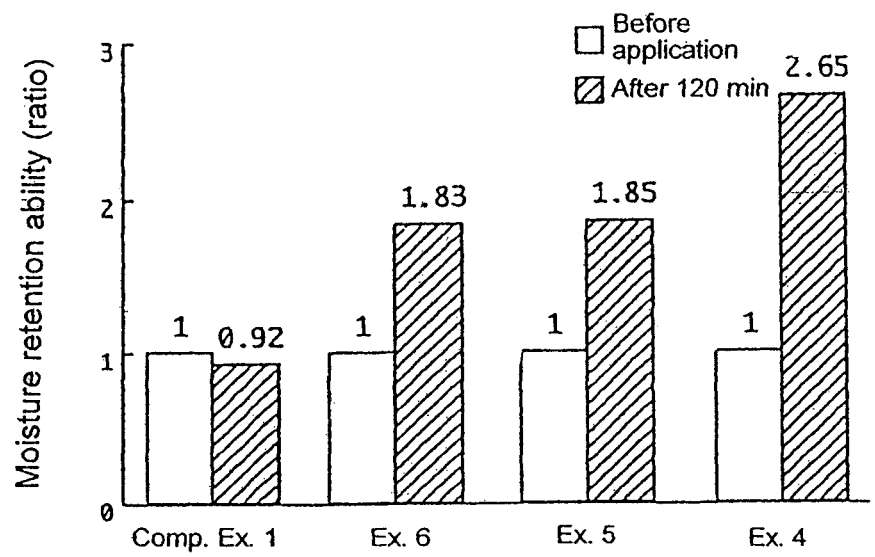
FIGS. 32 to 34 show the results a moisture retention ability test performed on atopic skin according to embodiments of the present invention.
Figure 33:
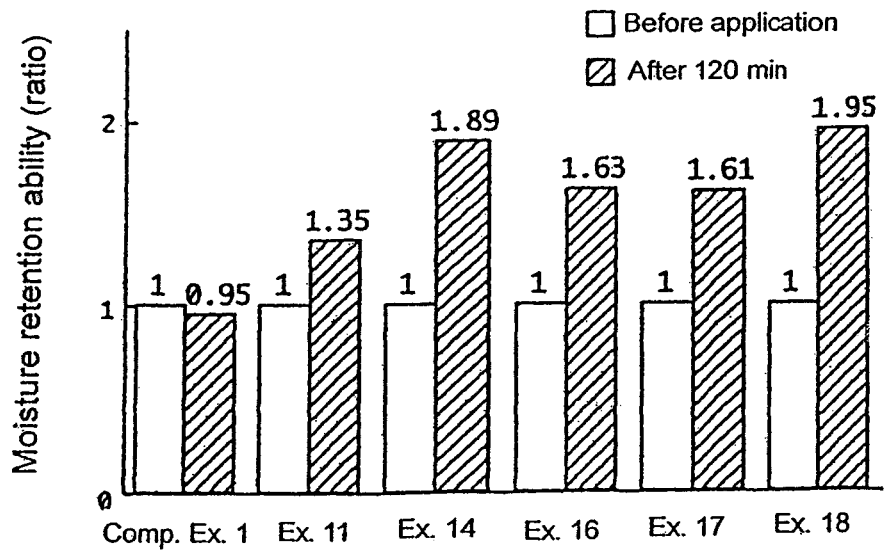
Figure 34:
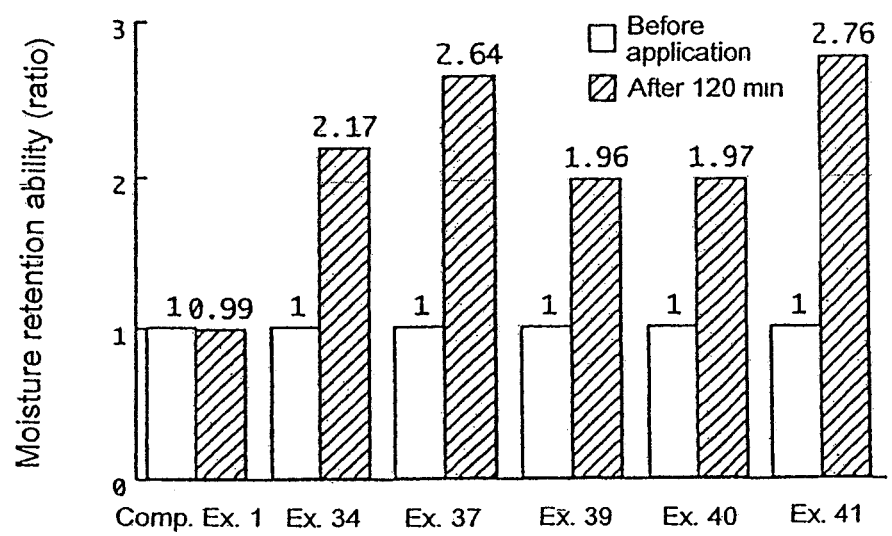

The results of the moisture retention ability test are as shown in FIGS. 32 through 34.

Although effects that increased moisture retention ability for atopic skin were not observed at all for Comparative Example 1, the moisture retention ability 2 hours after applying the samples of the above-mentioned embodiments of the present invention increase significantly as compared with before application.

In FIG. 32, although moisture retention ability increased with either L-arginine alone (Example 4) or ethanolamine alone (Example 5), in the case both substances were present (Example 6), moisture retention ability was increased more than when either substance was used alone even at lower concentrations.

Although Examples 34 through 41 (referred to as the "former") are mixtures of rice preparations containing 0.03% L-arginine with Examples 11 through 18 (referred to as the "latter"), respectively, the former demonstrated higher moisture retention ability than the latter (FIG. 34).

In this manner, the samples of the present invention increased the skin's barrier function by acting on the corneal layer, and acted on epidermal keratocytes not present in the corneal layer to produce a corneal layer having a high barrier function.

TEST EXAMPLE 11

The amount of moisture loss from the skin (transepidermal moisture evaporation volume) was measured to confirm barrier function improvement effects.

Panelists: 4 persons with atopic skin
Test Method: Each sample was applied to the side of the forearm of the panelists (approx. 0.3×0.3 cm) followed by measurement of transepidermal moisture evaporation volume at 60 and 120 minutes after application.
Measurement Method:
(1) The test site is washed with soap.
(2) The test site is exposed in a constant temperature and constant humidity room at a temperature of 20° C. and humidity of 50%, and the skin is allowed to reach a steady state by allowing the panelists to rest quietly starting 60 minutes before measurement.
(3) Transepidermal water loss (TWEL) at the test site is measured for about 1 minute (the rate of moisture evaporation at the test site is measured as TEWL ($g/m^2 h$) automatically by software computation by contacting a cylindrical probe of the TEWAMETER TM210 perpendicular to the test site).

Figure 35:
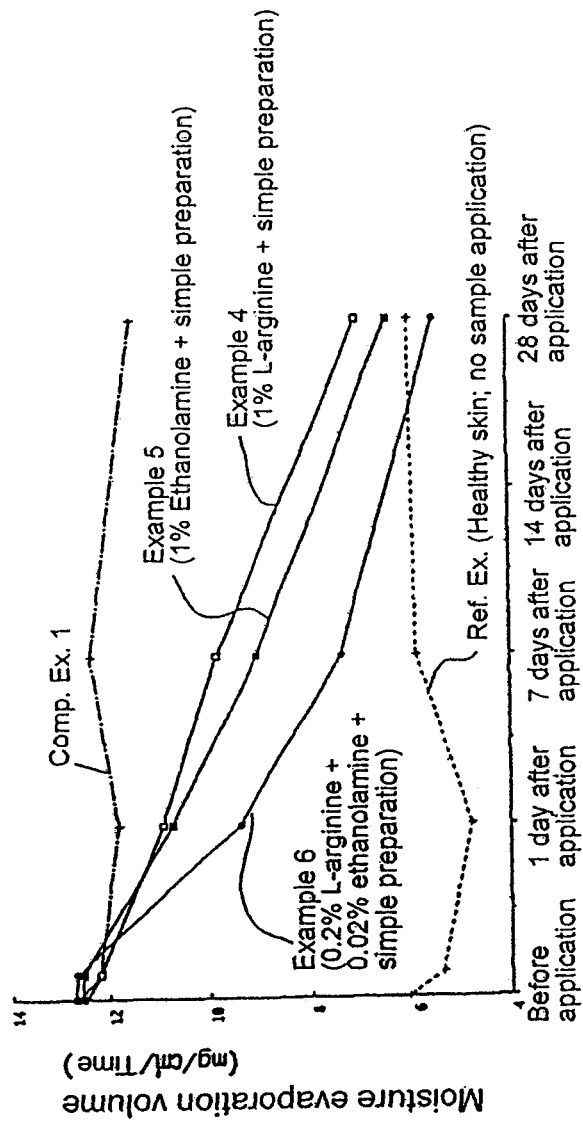
FIGS. 35 to 37 show the results of a test of transepidermal moisture evaporation volume performed on atopic skin according to embodiments of the present invention.
Figure 36:
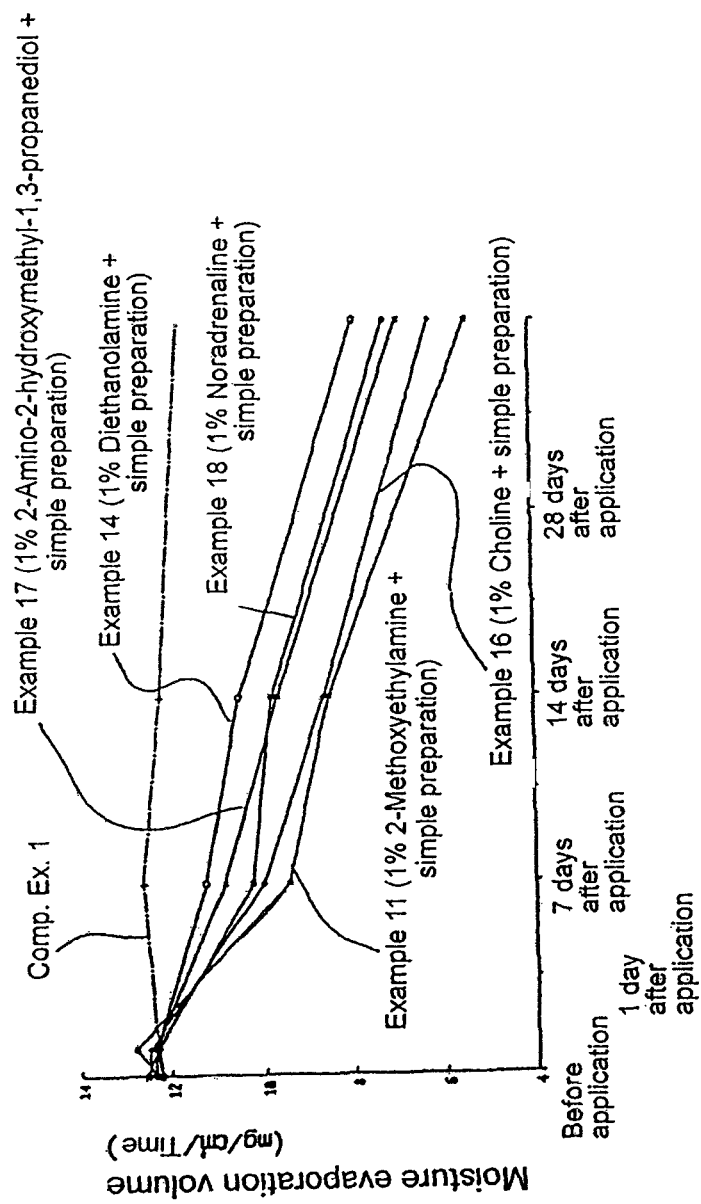

Test Apparatus:
TEWAMETER TM210 (Nippon Eurotech)
TEWAMETER Software Ver. 1.1 (Nippon Eurotech)
Samples: Same as the samples used in Test Example 10
The test results for transepidermal moisture evaporation volume are as shown in FIGS. 35 through 37.

The amount of moisture loss is greater in atopic skin prior to application of the samples of the present invention as compared with healthy skin due to a decrease in the skin's barrier function. The amount of moisture loss was decreased nearly to the level of healthy skin following application of the samples of the present invention to atopic skin for 4 weeks, and the skin's barrier mechanism and function were determined to have been improved.

Figure 37:
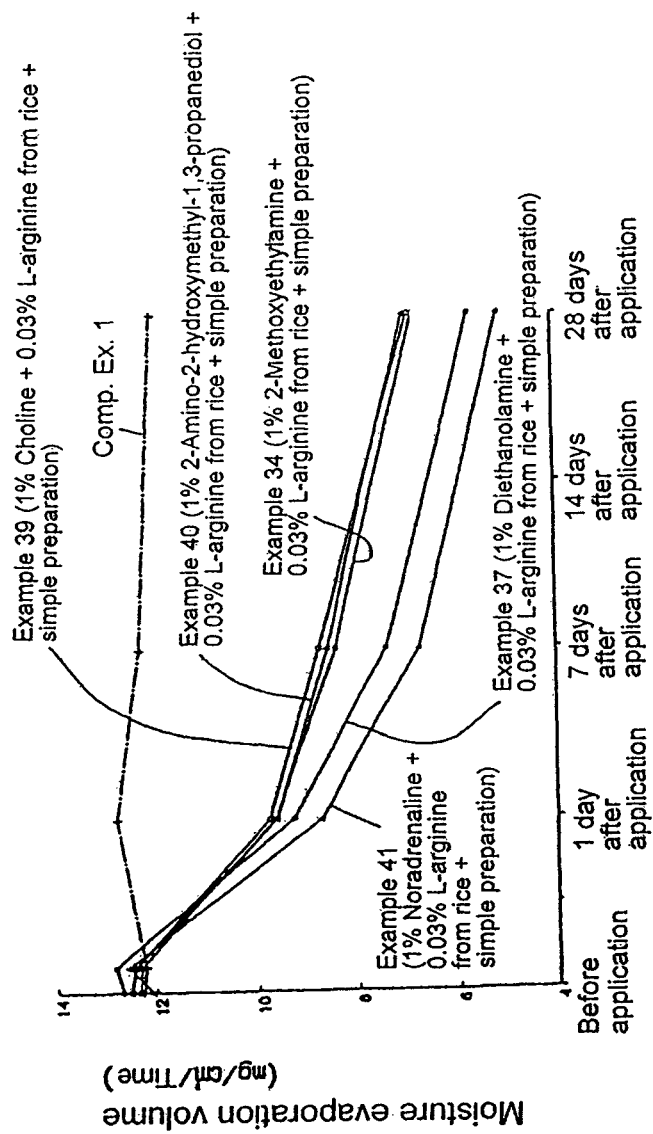

Although Examples 34 through 41 (referred to as the "former") are mixtures of rice preparations containing 0.03% L-arginine with Examples 11 through 18 (referred to as the "latter"), respectively, the former demonstrated greater effects that reduced the amount of moisture loss than the latter (FIG. 37).

In this manner, impairment of the skin's barrier mechanism and function was improved, and internal moisture loss was inhibited by applying the samples of the present invention to atopic skin.

TEST EXAMPLE 12

An allergic reaction inhibition test was conducted in house dust-sensitized model animals (guinea pigs).

Experimental Animals: Guinea pigs, 6
Test Method:
(1) House dust extract and adjuvant were mixed and injected subcutaneously into the guinea pigs to sensitize.
(2) After sensitization was established, the abdomens of the guinea pigs were shaved to produce chapped skin.
(3) The samples were applied to the site where chapped skin was produced.
(4) House dust extract was applied to the sample application site.
(5) Skin reaction was evaluated for 1-5 days after step (4).

Evaluation of the induced skin reaction (dermatitis) was scored based on the following standards.
0: No reaction
1: Mild erythema
2: Moderate erythema
3: Serious erythema
4: Serious erythema accompanied by edema
The samples were as shown below.

EXAMPLE 55

Simple Preparation Containing 40% Example 3

| | |
|---|---|
| Example 3 (containing 0.2% L-arginine and 0.02% ethanolamine from rice) | 40.00 mL |
| 95% ethanol | 2.00 mL |
| Parabenzene | 0.18 g |
| Purified soy bean lecithin | 0.05 g |

Brought to a total weight of 100.00 g by addition of purified water.

COMPARATIVE EXAMPLE 1

Simple Preparation

Figure 38:
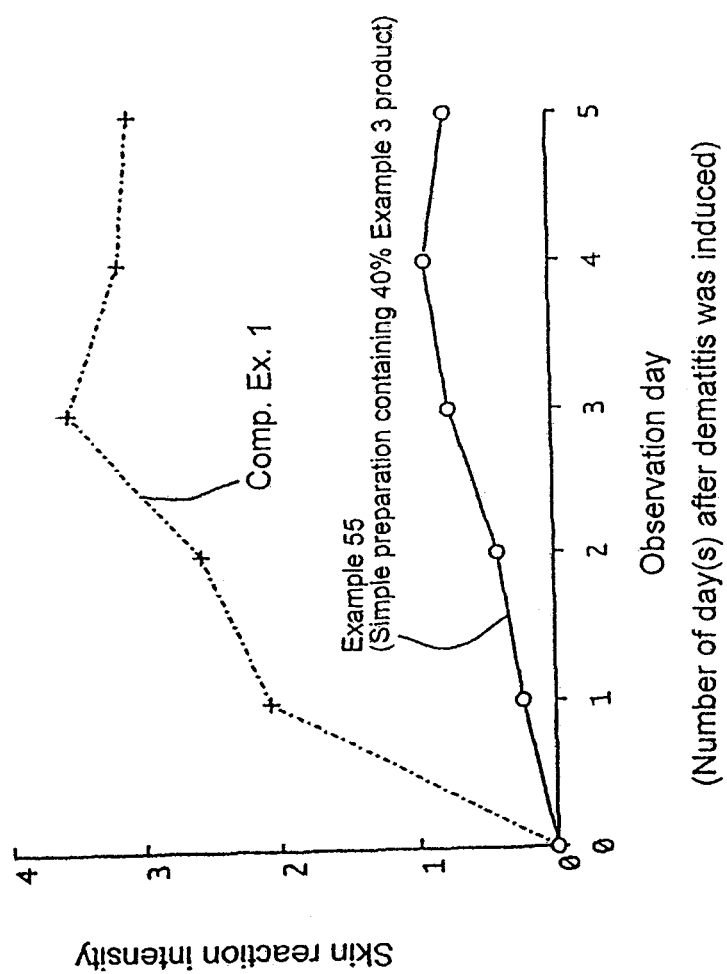
FIG. 38 shows the results of an allergic reaction inhibition test according to embodiments of the present invention.
Figure 39:
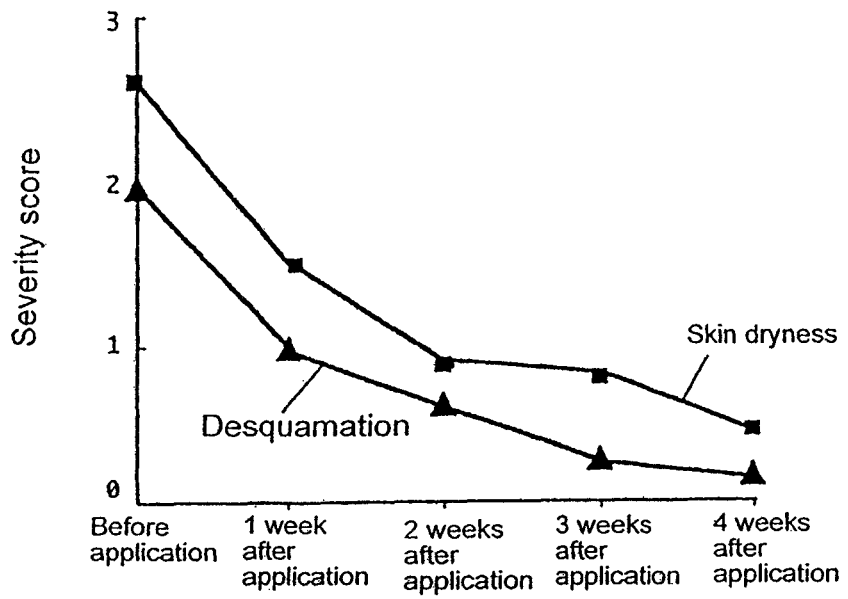
FIGS. 39 to 50 show changes in the severity score performed on atopic skin according to embodiments of the present invention.
Figure 40:
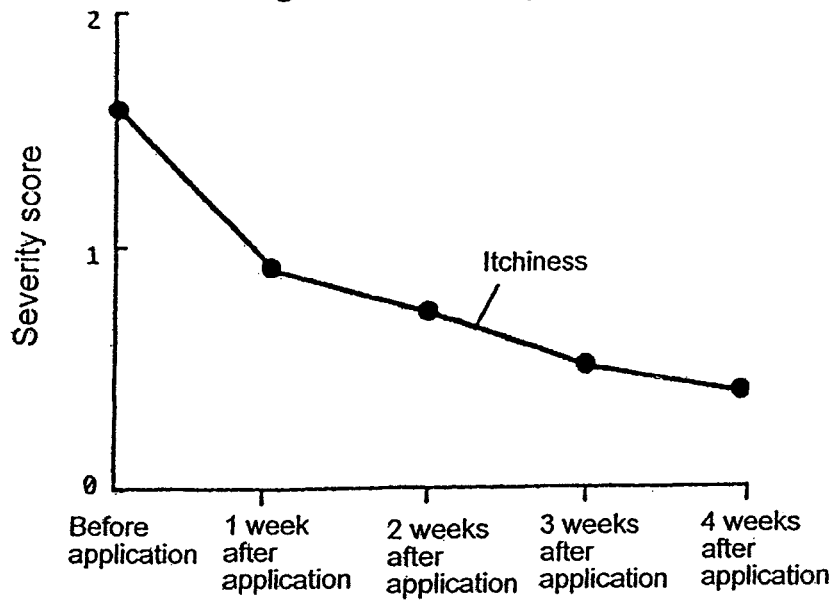
Figure 41:
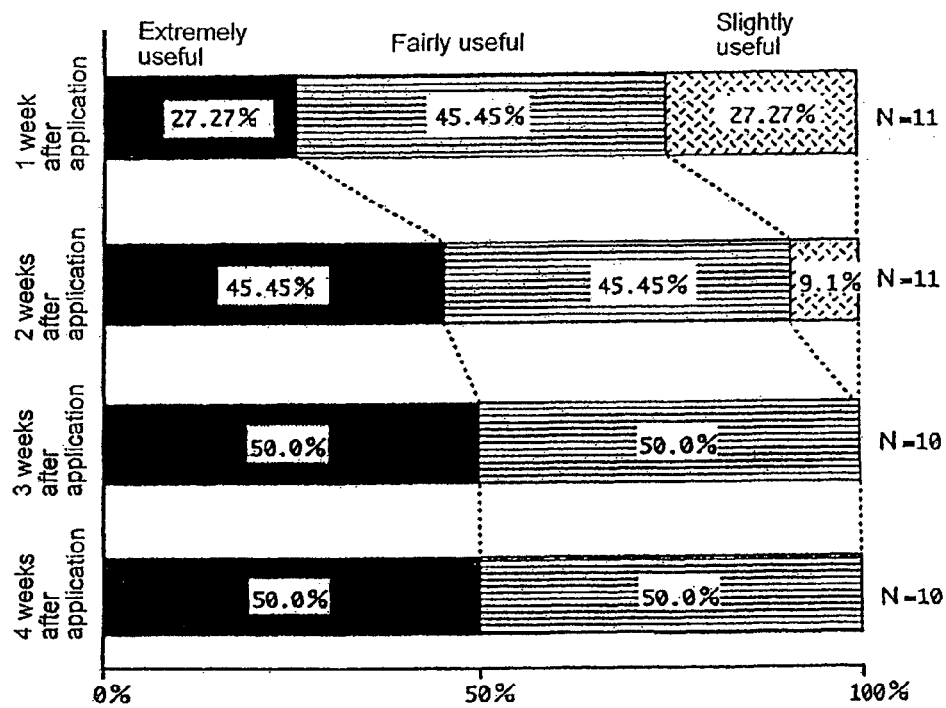
Figure 42:
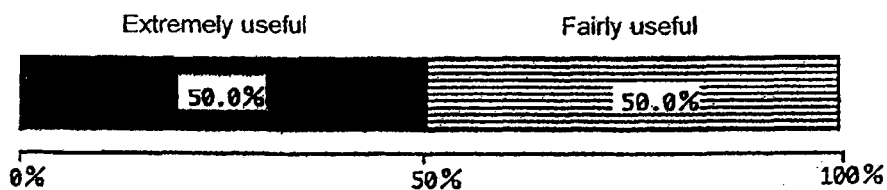
Figure 43:
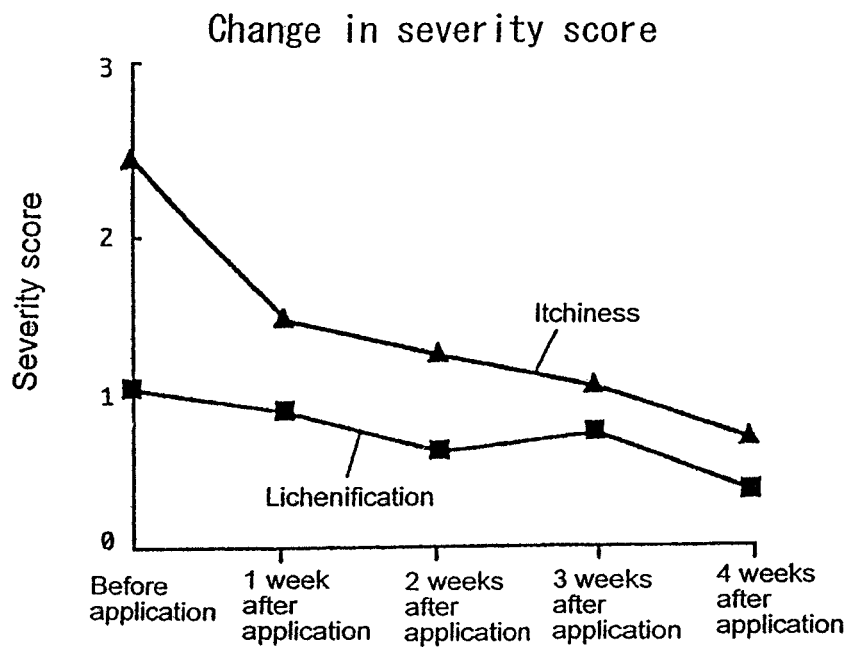
Figure 44:
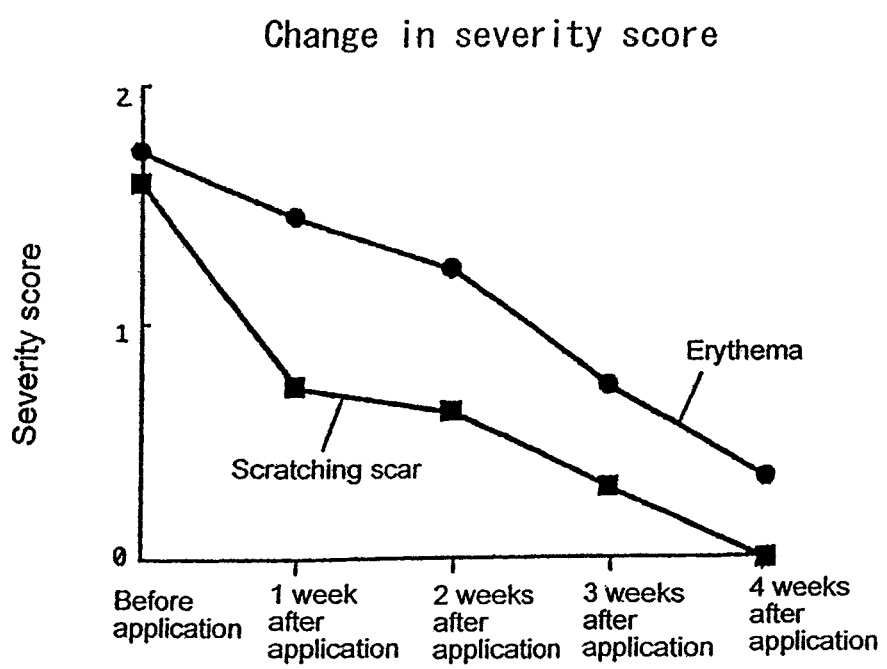
Figure 45:
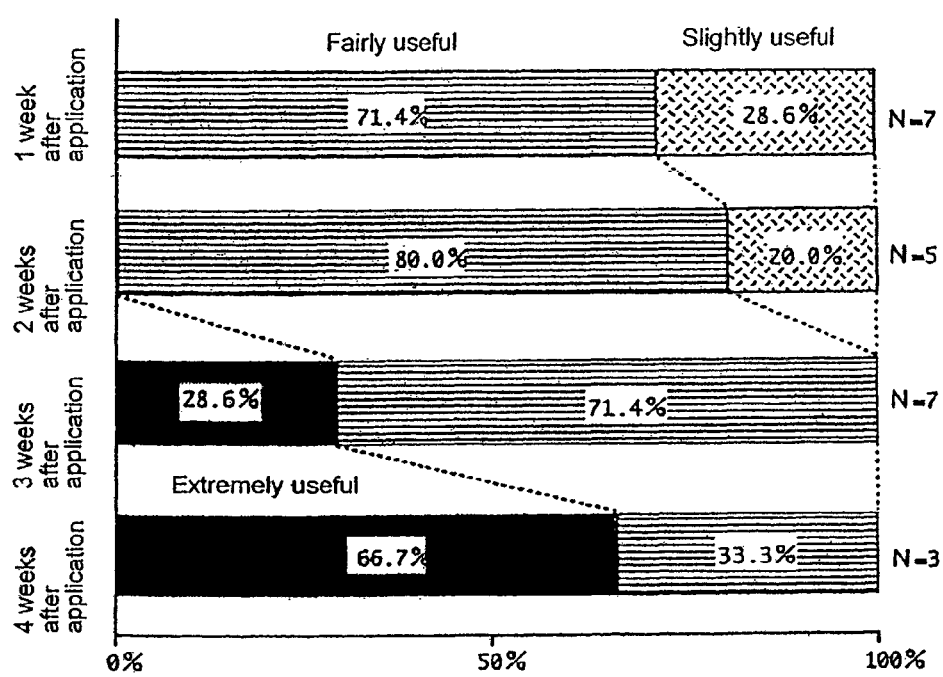
Figure 46:
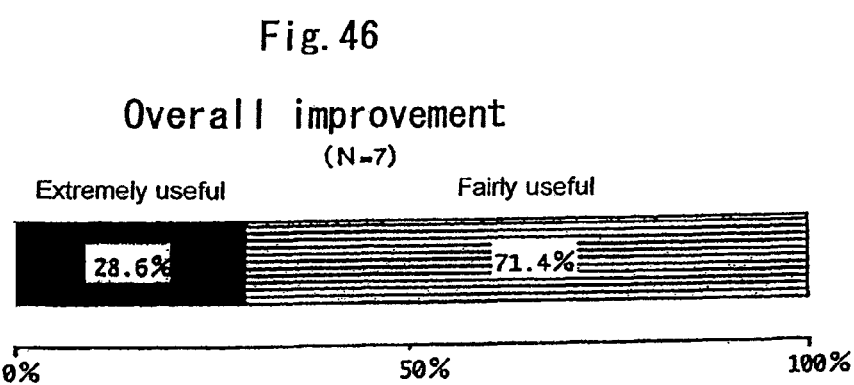
Figure 47:
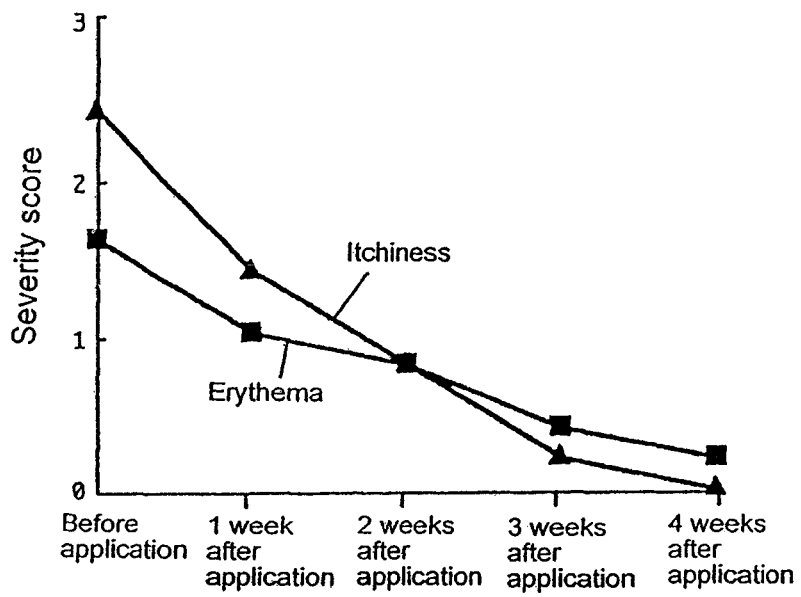
Figure 48:
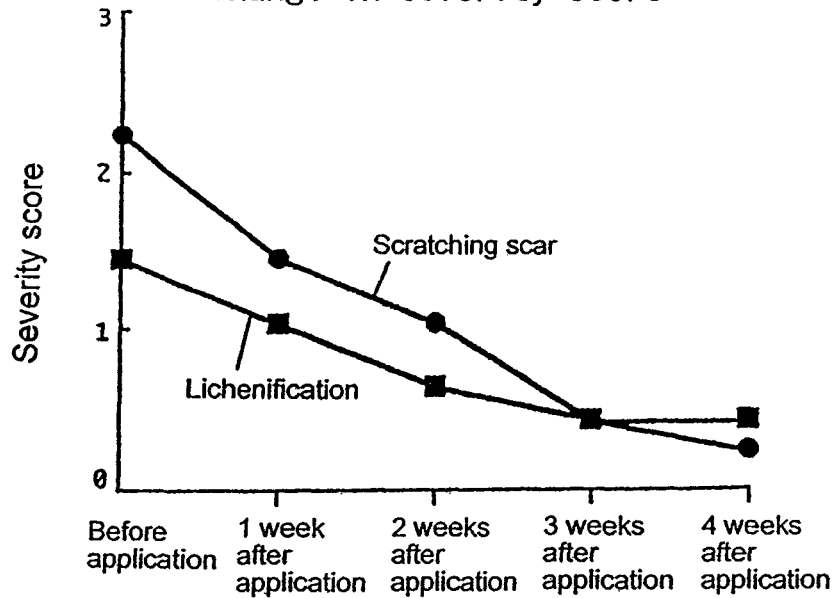
Figure 49:
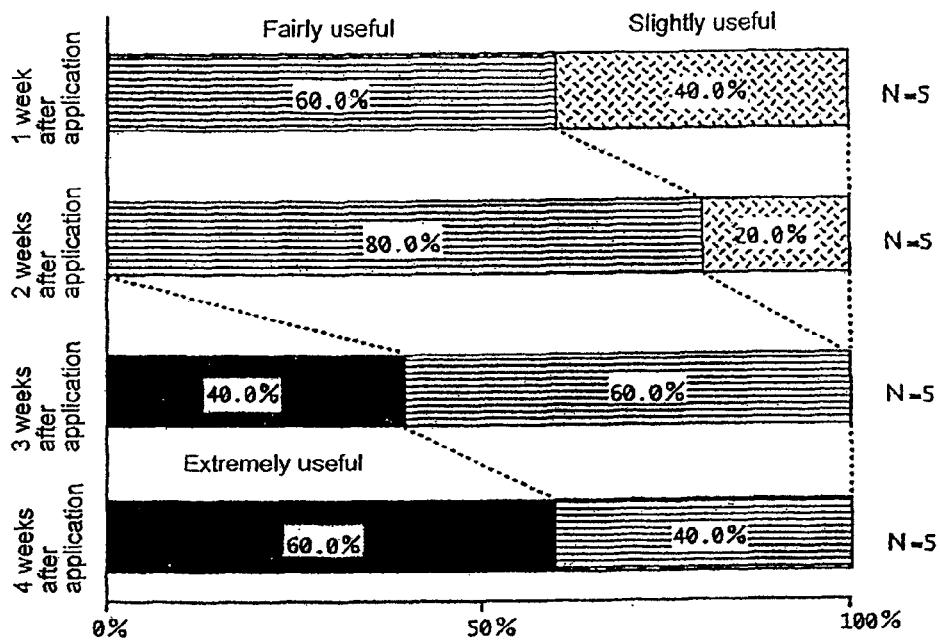
Figure 50:
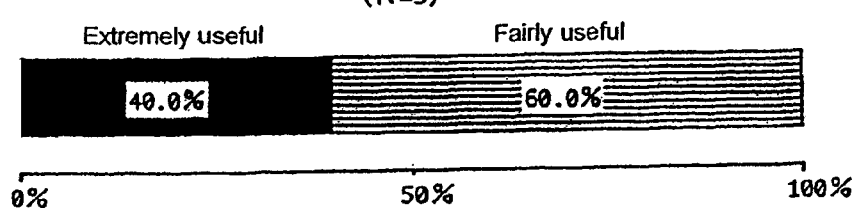

The results of the allergic reaction inhibition test in house dust-sensitized model animals (guinea pigs) are shown in FIG. 38.

When a sample of the present invention was applied to house dust-sensitized guinea pig skin in which chapped skin had been produced artificially followed by reapplication of house dust, the degree of house dust extract-induced dermatitis was inhibited over the course of 5 days after application.

In this manner, skin in which impairment of the skin's barrier mechanism and function was improved by application of a sample of the present invention was able to prevent infiltration of antigen from the outside and inhibit dermatitis.

TEST EXAMPLE 13

A clinical test was conducted on atopic skin of patients with atopic dermatitis.
Panelists: 12 patients with atopic dermatitis
Test Sites:
The test sites consisted of sites having symptoms suitable for evaluation that enabled comparison of a site using Example 8 and a site using Comparative Example 5 either to the left and right or above and below.
External Application Method:
Simple application at each site separately for Example 8 and Comparative Example 5 twice per day (morning and evening).
Application Period: 4 weeks
Evaluation Items:
Evaluation items consisted of the main symptoms of atopic skin.
(1) Skin dryness
(2) Scaling
(3) Itchiness
Evaluation Method:
The results of the site where Example 8 was applied were evaluated for the evaluation items according to the following four levels of a severity score as determined by visual examination.

3: Advanced symptoms
2: Moderate symptoms
1: Mild symptoms
0: No symptoms or symptoms disappeared In addition, improvement (usefulness) of effects as compared with Comparative Example 5 was evaluated each week according to the following four levels:
Extremely useful
Useful
Somewhat useful
Not useful Finally, the usefulness of the present invention was evaluated in terms of the overall usefulness throughout the usage period.
The samples were as shown below.

EXAMPLE 8

Example 3+Cream Preparation

| | |
|---|---|
| Example 3 (containing 0.2% L-arginine and 0.02% ethanolamine from rice) | 40.00 mL |
| Dipotassium glycyrrhetinate | 0.10 g |
| 1,3-butyleneglycol | 6.00 g |
| Concentrated glycerin | 6.00 g |
| Methylpolysiloxane | 6.00 g |
| Stearic acid | 3.00 g |
| Cetanol | 3.00 g |
| Cetyl 2-ethylhexanoate | 6.00 g |
| Squalene | 6.00 g |
| Sucrose fatty acid ester | 3.00 g |
| dl-α-tocopherol acetate | 0.30 g |
| Sodium casein | 1.50 g |
| Disodium edetate | 0.03 g |
| Parabenzene | 0.30 g |

Brought to a final weight of 100.00 g by addition of purified water.

COMPARATIVE EXAMPLE 5

Cream Preparation

| | |
|---|---|
| Dipotassium glycyrrhetinate | 0.10 g |
| 1,3-butyleneglycol | 6.00 g |
| Concentrated glycerin | 6.00 g |
| Methylpolysiloxane | 6.00 g |
| Stearic acid | 3.00 g |
| Cetanol | 3.00 g |
| Cetyl 2-ethylhexanoate | 6.00 g |
| Squalene | 6.00 g |
| Sucrose fatty acid ester | 3.00 g |
| dl-α-tocopherol acetate | 0.30 g |
| Sodium casein | 1.50 g |
| Disodium edetate | 0.03 g |
| Parabenzene | 0.30 g |

Brought to a final weight of 100.00 g by addition of purified water.
Test Results:

When a sample of the present invention and Comparative Example 5 were respectively used on skin susceptible to the induction of dermatitis (atopic skin) located near to the affected area of atopic dermatitis patients, in contrast to Comparative Example 5 being completely ineffective, the present invention demonstrated a high degree of usefulness.

FIGS. 39 through 42 show the changes in severity scores of skin dryness, scaling and itchiness. According to these results, the present invention alleviated skin symptoms such as skin dryness, scaling and itchiness associated with atopic dermatitis, and was observed to demonstrate a high degree of usefulness against each of these symptoms. There were no adverse side effects observed and a high degree of safety was observed.

Since the present invention has remarkable effects against itchiness, the vicious circle of itchiness leading to scratching, scratching leading to increased itchiness, and further scratching leading to exacerbation of atopic dermatitis can be terminated, thereby making it possible to prevent the onset and exacerbation of atopic dermatitis. In addition, as a result of being freed from itchiness, the present invention also has effects on the mental state of atopic dermatitis patients.

In this manner, the present invention is able to improve skin symptoms of skin dryness, scaling and itchiness observed in atopic skin, thereby being able to prevent the onset and exacerbation of atopic dermatitis, by restoring the skin's barrier mechanism and function through conditioning of the skin.

TEST EXAMPLE 14

A clinical test was conducted on the affected skin of atopic dermatitis patients to observe the therapeutic effects on atopic dermatitis as a result of skin conditioning and restoration of the skin's barrier mechanism and function.
Panelists: 7 patients with atopic dermatitis
Samples: Sample as in the case of Test Example 13.

EXAMPLE 8

Example 3+Cream Preparation

COMPARATIVE EXAMPLE 5

Cream Preparation

Test Sites:
The test sites consisted of sites having symptoms suitable for evaluation that enabled comparison of a site using Example 8 and a site using Comparative Example 5 either to the left and right or above and below.
External Application Method:
Simple application at each site separately for Example 8 and Comparative Example 5 twice per day (morning and evening).
Application Period: 4 weeks
Evaluation Items:
Evaluation items consisted of the following:
(1) Itchiness
(2) Dry marks
(3) Erythema
(4) Lichenification
Evaluation Method:
The results of the site where Example 8 was applied were evaluated for the evaluation items according to the following four levels of a severity score as determined by visual examination.
  3: Advanced symptoms
  2: Moderate symptoms
  1: Mild symptoms
  0: No symptoms or symptoms disappeared
In addition, improvement (usefulness) of effects as compared with Comparative Example 5 was evaluated each week according to the following four levels:
  Extremely useful
  Useful
  Somewhat useful
  Not useful
Finally, the usefulness of the present invention was evaluated in terms of the overall usefulness throughout the usage period.
Test Results:

When a sample of the present invention and Comparative Example 5 were respectively used on atopic dermatitis patients, in contrast to Comparative Example 5 being completely ineffective, the present invention demonstrated a high degree of usefulness as shown in FIGS. 43 through 46.

FIGS. 43 through 46 show the changes in severity scores of itchiness, dry marks, erythema and lichenification at the site of use of Example 8 of the present invention. According to these results, the present invention alleviated skin symptoms such as itchiness, dry marks, erythema and lichenification associated with atopic dermatitis, and was observed to demonstrate a high degree of usefulness against each of these symptoms. There were no adverse side effects, rebound phenomena were not observed following discontinuation of use, and there were no cases of recurrence.

Since the present invention has remarkable effects against itchiness, the vicious circle of itchiness leading to scratching and scratching leading to exacerbation of atopic dermatitis can be terminated, and it is possible to prevent the onset and exacerbation of atopic dermatitis. In addition, as a result of being freed from itchiness, the present invention also has effects on the mental state of atopic dermatitis patients.

In this manner, the present invention is able to improve skin symptoms of itchiness, dry marks, erythema and lichenification observed in atopic dermatitis, thereby being able to heal this disease, through conditioning of the skin.

TEST EXAMPLE 15

A clinical test was conducted on the affected skin of atopic dermatitis patients to observe the therapeutic effects on atopic dermatitis as a result of skin conditioning and restoration of the skin's barrier mechanism and function.
Panelists: 5 patients with atopic dermatitis
Samples:

EXAMPLE 56

1% Ethanolamine+Cream Preparation

| | |
|---|---|
| Ethanolamine (Nakarai Tesk) | 1.00 g |
| Dipotassium glycyrrhizin | 0.10 g |
| 1,3-butyleneglycol | 6.00 g |
| Concentrated glycerin | 6.00 g |
| Methylpolysiloxane | 6.00 g |
| Stearic acid | 3.00 g |
| Cetanol | 3.00 g |
| Cetyl 2-ethylhexanoate | 6.00 g |
| Squalene | 6.00 g |
| Sucrose fatty acid ester | 3.00 g |
| dl-α-tocopherol acetate | 0.30 g |
| Sodium casein | 1.50 g |
| Disodium edetate | 0.03 g |
| Parabenzene | 0.30 g |

Brought to a final weight of 100.00 g by addition of purified water.

COMPARATIVE EXAMPLE 5

Cream Preparation

Test Sites:
The test sites consisted of sites having symptoms suitable for evaluation that enabled comparison of a site using Example 56 and a site using Comparative Example 5 either to the left and right or above and below.

External Application Method:
Simple application at each site separately for Example 56 and Comparative Example 5 twice per day (morning and evening).

Application Period: 4 weeks
Evaluation Items: Same as Test Example 13.
Evaluation Method: Same as Test Example 13.
Test Results:

When Example 56 of the present invention and Comparative Example 5 were respectively used on atopic dermatitis patients, in contrast to Comparative Example 5 being completely ineffective, Example 56 of the present invention demonstrated a high degree of usefulness as shown in FIGS. 47 through 50.

FIGS. 47 through 50 show the changes in severity scores of itchiness, dry marks, erythema and lichenification at the site of use of Example 56 of the present invention. According to these results, Example 56 of the present invention alleviated skin symptoms such as itchiness, dry marks, erythema and lichenification associated with atopic dermatitis, and was observed to demonstrate a high degree of usefulness against each of these symptoms. There were no adverse side effects, rebound phenomena were not observed following discontinuation of use, and there were no cases of recurrence.

Since the present invention has remarkable effects against itchiness, the vicious circle of itchiness leading to scratching and scratching leading to exacerbation of atopic dermatitis can be terminated, and it is possible to prevent the onset and exacerbation of atopic dermatitis. In addition, as a result of being freed from itchiness, the present invention also has effects on the mental state of atopic dermatitis patients.

In this manner, the present invention is able to improve skin symptoms of itchiness, dry marks, erythema and lichenification observed in atopic dermatitis, thereby being able to heal this disease, through conditioning of the skin.

The moisture retention agent used in the present invention contains one or more types of substances selected from the group consisting of polyvalent alcohols represented by glycerin, dipropyleneglycol and 1,3-butyleneglycol; sugars represented by sorbitol, maltitol, dextrin, hyaluronic acid and chitosan; mucopolysaccharides and sugar derivatives; polypeptides represented by elastin and collagen; organic acids and their salts represented by pyrrolidone carboxylic acid, citric acid and lactic acid; biopharmaceutical and natural moisture retention agents represented by refined rice wine, rice bran, aloe, ????? and chamomile; bio-component moisture retention agents represented by vitamins, placental extract, urea, lecithin, phospholipid, seramide, cholesterol and sphingolipid; and, vegetable extracts, fruit extracts, kelp extracts, enzymes and inorganic salts; and, is one or more substances selected from the group consisting of animal oils, vegetable oils, hydrocarbons, higher alcohols and esters.

Drugs that can be used in pharmaceuticals, over-the-counter medicines and cosmetics which are externally applied skin preparations as claimed in the present invention are one or more types of substances selected from the group consisting of bactericidal drugs, wound protective agents, wound healing agents, drugs for suppurative diseases, analgesic, anti-itching, astringent and antiphlogistic agents, immunosuppresants, drugs for parasitic skin diseases, skin softeners, hair agents, vitamin agents and biopharmaceuticals, while the bases are one or more types of substances selected from the group consisting of moisture retention agents, astringents, refrigerants, antioxidants, ultraviolet absorbers, infrared dispersants, preservatives, antibiotics, chelating agents, surfactants, foaming agents, stabilizers, penetrants, assistants, pH adjusters, buffers, emulsifiers, opacefiers, fragrances and pigments.

The dry skin symptoms which are targets of the present invention are symptoms selected from atopic skin, dry or rough skin, aged skin, ichthyosis, dry skin, chapped skin, asteatosis, xeroderma, dry eczema, facial dry eczema and progressive volar keratoderma, and/or selected from erythema, induration and cornification, cracking, scaling, wrinkles, itching and dry marks, while skin aging symptoms are selected from wrinkles and decreased skin tightness and elasticity, skin damage caused by ultraviolet rays is selected from spots and freckles, skin disorders arising from the epidermis are selected from turnover abnormalities, fineness and moistness, physicochemical skin disorders are selected from cuts, burns and floor burns, biological skin disorders are selected from athlete's foot and skin infections, while dermatitis and eczema are inflammatory cornification disorders (psoriasis).

The present invention demonstrates remarkable effectiveness in the prevention and treatment of skin diseases such as atopic dermatitis, dry skin symptoms, pruritis, frostbite, cracking, chapped skin, skin aging symptoms, skin damage caused by ultraviolet rays, darkening, blackening, skin disorders arising in the epidermis, physicochemical skin disorders, skin symptoms caused by the use of water, soap, detergents, surfactants or solvents, adverse side effects of externally applied skin preparations, biological skin disorders, dermatitis, eczema and other skin diseases.

Potential Industrial Utilization

The present invention relates to a skin conditioner comprising the compound represented with the general formula (1):

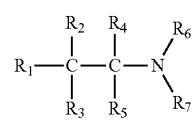

(1)

(wherein, the symbols are the same as those defined in the text). Examples of active ingredients of the present invention include L-arginine and ethanolamine. These active ingredients can be acquired as chemical synthesis products, or they may also be acquired in the form of natural substances. Preferable examples of natural substances include substances containing L-arginine and/or ethanolamine obtained from rice. The skin conditioner as claimed in the present invention demonstrates remarkable effectiveness as an agent for the prevention and treatment of atopic dermatitis and as a skin moisture retention agent.

The invention claimed is:
1. A method of improving moisture retention of skin and/or treating a skin condition in a subject in need thereof comprising applying to the skin of said subject a composition comprising an effective amount of a fermented rice preparation, wherein the fermented rice preparation contains 0.2 wt % L-arginine and 0.02 wt % of ethanolamine, and is prepared by a process comprising:
  crushing rice and hydrating the crushed rice with water to obtain an aqueous mixture;
  adding alpha-amylase, beta-amylase, acidic protease and acidic carboxypeptidase to the aqueous mixture for a sufficient time to allow the aqueous mixture to enzymatically react to obtain an enzymatically-treated mixture; and
  adding *Aspergillus orzae* and *Saccharomyces cerevicae* to the enzymatically-treated mixture for a sufficient time to allow fermentation of the enzymatically-treated mixture to obtain said fermented rice preparation;
  wherein the skin condition is selected from the group consisting of atopic dermatitis, dermatitis, eczema, dry skin, cracking skin, chapped skin, skin aging, skin damage caused by ultraviolet rays, scaling skin, wrinkles, itching and dry marks, decreased skin tightness and elasticity, and age spots.

2. The method according to claim 1, wherein the composition further comprises a moisture retention agent.

3. The method according to claim 2, wherein the moisture retention agent is one or more substances selected from the group consisting of polyvalent alcohols represented by glycerin, dipropylene glycol and 1,3-butylene glycol, sorbitol, maltitol, dextrin, hyaluronic acid, chitosan, mucopolysaccharides, elastin, collagen, pyrrolidone carboxylic acid, citric acid, lactic acid, refined rice wine, rice bran, aloe, licorice (sweet root), chamomile, vitamins, placental extract, urea, lecithin, phospholipid, seramide, cholesterol, sphingolipid, vegetable extracts, fruit extracts, kelp extracts, enzymes, animal oils, and vegetable oils.

4. The method according to claim 1, wherein the composition further comprises a drug.

5. The method according to claim 4, wherein the drug is one or more substances selected from the group consisting of bactericidal drugs, wound protective agents, wound healing agents, drugs for suppurative diseases, analgesic, anti-itching, astringent and antiphlogistic agents, immunosuppresants, drugs for parasitic skin diseases, skin softeners, hair agents, vitamin agents and biopharmaceuticals.

* * * * *